(12) United States Patent
Friedlander et al.

(10) Patent No.: US 7,419,953 B2
(45) Date of Patent: Sep. 2, 2008

(54) SELECTIVE R-CADHERIN ANTAGONIST AND METHODS

(75) Inventors: Martin Friedlander, Del Mar, CA (US); Michael I. Dorrell, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 554 days.

(21) Appl. No.: 10/836,289

(22) Filed: Apr. 30, 2004

(65) Prior Publication Data

US 2005/0004013 A1 Jan. 6, 2005

Related U.S. Application Data

(60) Provisional application No. 60/467,188, filed on May 1, 2003.

(51) Int. Cl.
*A61K 38/00* (2006.01)
(52) U.S. Cl. .......................................... 514/9
(58) Field of Classification Search ........................ None
See application file for complete search history.

(56) References Cited

U.S. PATENT DOCUMENTS

2002/0151681 A1* 10/2002 Rosen et al. ................. 530/350
2006/0057135 A1* 3/2006 Briskin et al. ............ 424/130.1

FOREIGN PATENT DOCUMENTS

WO    WO 96/24673    *  8/1996

OTHER PUBLICATIONS

Magdolen, Viktor, et al, "Cyclo19,31[D-Cys19]-uPA19-31 is a potent competitive antagonist of the interaction of urokinase-type plasminogen activator with its receptor (CD87)," Biological Chemistry (2001), 382(8), 1197-1205.*

* cited by examiner

*Primary Examiner*—Cecilia J. Tsang
*Assistant Examiner*—Thomas S. Heard
(74) *Attorney, Agent, or Firm*—Olson & Cepuritis, Ltd.

(57) ABSTRACT

An isolated peptide useful as a selective antagonist of mammalian R-cadherin comprises 3 to 30 amino acid residues, three contiguous residues of the peptide having the amino acid sequence Ile-Xaa-Ser; wherein Xaa is an amino acid residue selected from the group consisting of Asp, Asn, Glu, and Gln. Preferably Xaa is Asp or Asn. In one preferred embodiment the peptide is a cyclic peptide having 3 to 10 amino acid residues arranged in a ring. The selective R-cadherin antagonist peptides of the invention are useful for inhibiting the targeting of stem cells, such as endothelial precursor cells, to developing vasculature, for inhibiting R-cadherin mediated cellular adhesion, and for inhibiting retinal angiogenesis.

2 Claims, 12 Drawing Sheets

Human R-cadherin preproprotein variant

```
  1 mtagagvlll llslsgalra hnedlttret ckagfseddy talisqnile gekllqvkfs
 61 scvgtkgtqy etnsmdfkvg adgtvfatre lqvpseqvaf tvtawdsqta ekwdavvrll
121 vaqtssphsg hkpqkgkkvv aldpspppkd tllpwpqhqn anglrrrkrd wvippinvpe
181 nsrgpfpqql vrirsdkdnd ipirysitgv gadqppmevf sidsmsgrmy vtrpmdreeh
241 asyhlrahav dmngnkvenp idlyiyvidm ndnrpefinq vyngsvdegs kpgtyvmtvt
301 andaddstta ngmvryrivt qtpqspsqnm ftinsetgdi vtvaagldre kvqqytvivq
361 atdmegnlny glsntataii tvtdvndnpp eftastfage vpenrvetvv anltvmdrdq
421 phspnwnavy riisgdpsgh fsvrtdpvtn egmvtvvkav dyelnrafml tvmvsnqapl
481 asgiqmsfqs tagvtisimd ineapyfpsn hklirleegv ppgtvlttfs avdpdrfmqq
541 avrysklsdp aswlhinatn gqittaavld reslytknnv yeatflaadn gippasgtgt
601 lqiylidind napellpkea qicekpnlna initaadadv dpnigpyvfe lpfvpaavrk
661 nwtitrlngd yaqlslrily leagmydvpi ivtdsgnppl sntsiikvkv cpcddngdct
721 tigavaaagl gtgaivaili cilliltmvl lfvmwmkrre kerhtkqlli dpeddvrdni
781 lkydeeggge edqdydlsql qqpeamghvp skapgvrrvd erpvgaepqy pirpmvphpg
841 digdfinegl raadndptap pydsllvfdy egsgstagsv sslnssssgd qdydylndwg
901 prfkkladmy gggeed
```

FIG. 2

Human R-cadherin preproprotein variant

```
  1  mtagagvlll  llslsgalra  hnedlttret  ckagfseddy  talisqnile  gekllqvkfs
 61  scvgtkgtqy  etnsmdfkvg  adgtvfatre  lqvpseqvaf  tvtawdsqta  ekwdavvrll
121  vaqtssphsg  hkpqkgkkvv  aldpspppkd  tllpwpqhqn  anglrrrkrd  wvippinvpe
181  nsrgpfpqql  virsdkdnd   ipirysitgv  gadqppmevf  sinsmsgrmy  vtrpmdreeh
241  asyhlrahav  dmngnkvenp  idlyiyvidm  ndnhpefing  vyncsvdegs  kpgtyvmtit
301  andaddstta  ngmvryrivt  qtpqspsqnm  ftinsetgdi  vtvaagwdre  kvqqytvivq
361  atdmegnlny  glsntataii  tvtdvndnps  eftastfage  vpensvetvv  anltvmdrdq
421  phspnwnavy  riisgdpsgh  fsvrtdpvtn  egmvtvvkav  dyelnrafml  tvmvsnqapl
481  asgiqmsfqs  tagvtisimd  ineapyfpsn  hklirleegv  ppgtvlttfs  avdpdrfmqq
541  avrysklsdp  aswlhinatn  gqittvavld  reslytknnv  yeatflaadn  gippasgtgt
601  lqiylidind  napellpkea  qicerpnlna  initaadadv  hpnigpyvfe  lpfvpaavrk
661  nwtitrlngd  yaqlslrily  leagmydvpi  ivtdsgnppl  sntsiikvkv  cpcddngdct
721  tigavaaagl  gtgaivaili  cililltmvl  lfvmwmkrre  kerhtkqlli  dpeddvreki
781  lkydeeggge  edqdydlsql  qqpeamghvp  skapgvrrvd  erpvgpepqy  pirpmvphpg
841  digdfinegl  raadndptap  pydsllvfdy  egsgstagsv  sslnssssgd  qdydylndwg
901  prfkkladmy  gggeed
```

FIG. 3

Murine (mus musculus) R-cadherin preproprotein variant

```
  1 mttgsvlpll llglsgalra hredltvrea ckagfseegy talispnvle gekllkvefs
 61 scvgtkgmqy etnsldfkvg adgtvfatre lkipseqvaf tvtarerqsa eqwaamvrll
121 vaqtssahse hkkgqtvald psqppndtll pwpqhqssgg lrrqkrdwvi ppinvpensr
181 gpfpqqlvri rsdkdndipi rysitgvgad qppmevfnid smsgrmyvtr pmdreerasy
241 hlrahavdmn gnkvenpidl yiyvidmndn rpefinqvyn gsvdegskpg tyvmtvtand
301 addsttangm vryrivtqtp qspsqnmfti nsetgdivtv aagldrekvq qytvivqatd
361 megnlnygls ntataiitvt dvndnppeft tstfageype nrietvvanl tvmdrdqphs
421 pnwnavyrii sgdpsghfsv rtdpvtnegm vtvvkavdye lnrafmltvm vsnqaplasg
481 iqmsfqstag vtisvtdvne apyfpsnhkl irleegvpag talttfsavd pdrfmqqavr
541 ysklsdpanw lhintsngqi ttaaildres lytknnvyea tflaadngip pasgtgtlqi
601 ylidindnap qllpkeaqic erpglnaini taadadmdpn igpyvfelpf ipttvrknwt
661 itrlngdyaq lslrilylea gvydvpiivt dsgnpplsnt svikvkvcpc dengdcttvg
721 avaaaglgtg aivailiciv illimvllfv vwmkrreker htkqllidpe ddvrdnilky
781 deegggeedq dydlsqlqqp eamehvlskt pgvrrvderp vgaepqypvr pvvphpgdig
841 dfineglraa dndptappyd sllvfdyegs gstagsvssl nsssgdqdy dylndwgprf
901 kkladmyggg eed
```

```
N-cad  (m)  24-IRSDRDKNLSLRYSVTGPGADQPPTGIFIINPISGQLSVTKPLDRELIARFHLRAHAVDINGNQVENPI-92
R-cad  (m)  24-IRSDKDNDIPIRYSITGVGADQPPMEVFNIDSMSGRMYVTRPMDREERASYHLRAHAVDMNGNKVENPI-92
R-cad  (r)  24-IRSDKDNDIPIRYSITGVGADQPPMEVFNIDSMSGRMYVTRPMDREERASYHLRAHAVDMNGNKVENPI-92
R-cad  (h1) 24-IRSDKDNDIPIRYSITGVGADQPPMEVFSIDSMSGRMYVTRPMDREEHASYHLRAHAVDMNGNKVENPI-92
R-cad  (h2) 24-IRSDKDNDIPIRYSITGVGADQPPMEVFSINSMSGRMYVTRPMDREEHASYHLRAHAVDMNGNKVENPI-92
R-cad  (c)  24-IRSDKDKEIHIRYSITGVGADQPPMEVFSIDPVSGRMYVTRPMDREERASYHLRAHAVDMNGNKVENPI-92
```

B

|  | Cyclic peptides | Linear peptides |
|---|---|---|
| R-cad specific peptides | Cyclic IDS  (CIDSC) | IDSMSGR |
|  |  | IDSASGR |
| N-cad specific peptides | Cyclic INP  (CINPC) | INPISGQ |
| Control peptides | Cyclic SDI  (CSDIC) |  |
|  | Cyclic RAD  (CRADC) |  |

FIG. 5

ND METHODS

CROSS REFERENCE TO RELATED APPLICATIONS

This application claims the benefit of U.S. Provisional Application for Patent Ser. No. 60/467,188, filed on May 1, 2003, which is incorporated herein by reference.

STATEMENT OF GOVERNMENT INTEREST

This invention was made with United States government support under Grants No. EY11254 and EY12598 from the National Institutes of Health. The United States government has certain rights in this invention.

FIELD OF THE INVENTION

This invention relates generally to antagonists of mammalian cellular adhesion molecules. More specifically, the invention relates to selective peptide antagonists of mammalian R-cadherin (cadherin-4) and methods of inhibiting cellular adhesion and retinal angiogenesis therewith.

BACKGROUND OF THE INVENTION

The cadherin family of molecules consists of transmembrane glycoproteins that function in calcium dependent, selective cell-cell interactions. These molecules play important roles during embryonic development and tissue morphogenesis by mediating cell recognition and cell sorting. Subfamilies of cadherins (classic cadherins, protocadherins, desmocollins, and other cadherin-related proteins) are characterized by variable numbers of extracellular cadherin domains, a single transmembrane segment, and a single cytoplasmic domain. The so-called classic cadherins (i.e., E, P, N, and R-cadherin) reportedly have five tandemly repeated extracellular cadherin domains (EC1-EC5) that engage in preferentially homophillic interactions, and a highly conserved cytoplasmic tail that mediates adhesion specific intracellular signaling.

Cadherin mediated cell-cell adhesions occur as multiple cadherin molecules expressed on adjacent cells interact, leading to the formation of adherens junctions. According to the cadherin zipper model proposed by Shapiro et al. *Nature* 1995; 374(6520):327-37, cadherin molecules within the membrane of the same cell form tight parallel-strand dimers (i.e., so-called cis-dimers). As illustrated in FIG. 1, these cis-dimers then bind to cadherin dimers expressed on adjacent cells (i.e., trans-dimerization). Once a sufficient interaction is sustained, cadherin clustering can occur as more cadherin molecules are recruited to the site, leading to interdigitation of molecules from the two-cell surfaces. In this manner, relatively weak interactions can combine to form fairly strong cell-cell adhesions.

Upon initial cadherin adhesion, intracellular signals, transmitted through interactions of the cytoplasmic cadherin tails with α and β catenin molecules, lead to reorganization of the cytoskeleton. Although the association with actin filaments is not thought to affect homophillic binding, their association helps hold the cadherin molecules at the sites of interaction. In a symbiotic-type of relationship, cadherin clustering causes reorganization of the cytoskeleton and provides points of attachment at the membrane, which are important for cellular changes that occur upon the formation of adherens junctions. Meanwhile, association with the cytoskeleton holds cadherins at the sites of interaction and helps recruit new cadherin molecules, thus mediating cadherin clustering. Calcium plays an important role as a cofactor during cadherin clustering. Cadherin function is lost and molecules become more susceptible to protease degradation in solutions with insufficient concentrations of calcium ions (i.e., below about 2 mM). This is due to the requirement of calcium to stabilize the structure of cadherin molecules and provide proper orientation of adjacent cadherin interfaces.

Although it is reported that each of the five extracellular classical cadherin domains EC1 through EC5 plays an important role in mediating cadherin dimerization, mutational analysis has suggested that the majority of residues that form the dimerization interface are found within the N-terminal most cadherin domain (EC1) (Kitagawa, et al., *Biochem. Biophys. Res. Commun.,* 2000; 271(2):358-63.). However, relatively little is known about the mechanisms of specific homodimerization between cadherin molecules.

Cadherins play a significant role during neuronal guidance and development of the central nervous system. Different subdivisions of the brain are reportedly defined by differential expression of cadherin types. Cadherins also play an important role in neural retinal development by specific expression within different regions of the developing retina. For example, during embryonic chick retina development, B-cadherin is reportedly only found in Müller glia, while certain populations of bipolar cells express R-cadherin (also known as cadherin-4). Amacrine cells and a subset of ganglion cells express cadherins 6B and 7. Within the inner plexiform layer of the retina, these same cadherins are only expressed in sublaminae associated with synapsin-I positive nerve terminals, suggesting that distinct expression profiles contribute to synapse formation between specific subpopulations of neurons during retina development. In the embryonic optic nerve, ganglion cell axon outgrowth is mediated by N-cadherin adhesion with R-cadherin-expressing glial cells.

Cadherin adhesion also plays a role in developmental retinal vascularization (Dorrell, et al. *Invest. Ophthalmol. Vis. Sci.* 2002; 43(11):3500-10). Disruption of R-cadherin adhesion during formation of the superficial vascular plexus results in the loss of complex vascular interconnections observed during normal vascular patterning. When R-cadherin adhesion is blocked during the subsequent formation of deep vascular layers, key guidance cues are lost causing the vessels to migrate past the normal deep vascular plexuses and into the photoreceptor layer.

The retina consists of well-defined layers of neuronal, glial, and vascular elements. Any disease or condition that alters the retinal layers even slightly, can lead to neuronal degeneration and significant visual loss. The retinal degeneration mouse (rd/rd mouse) has been investigated for over 70 years as a model for many diseases that lead to photoreceptor cell death. In the rd/rd mouse, photoreceptor degeneration begins during the first three weeks after birth as rod cells undergo apoptosis, attributed to a mutation in the β subunit of cGMP-dependent phosphodiesterase followed by cone photoreceptor death. Vascular atrophy within the retina is temporally associated with photoreceptor cell death in rd/rd mice as well. The vasculature appears to form in the normal characteristic fashion as three functional layers develop within the first three weeks. However, the vessels in the deep vascular layer begin to degenerate during the second week and by the end of the fourth postnatal week, dramatic vascular reduction is observed as the deep and intermediate plexuses nearly completely disappear.

A population of hematopoietic stem cells resides in the normal adult circulation and bone marrow, from which different sub-populations of cells can differentiate along lineage positive (Lin⁺HSC) or lineage negative (Lin⁻HSC) lineages. In addition, the present inventors have discovered that endothelial precursor cells (EPCs), capable of forming blood vessels in vitro and in vivo, are present within the Lin⁻HSC subpopulation. EPCs within the population of Lin⁻HSCs can target and stabilize the degenerating vasculature in rd/rd mice when injected intravitrally to the eyes of the mice. Intravitreally injected Lin⁻HSCs target astrocytes in the superficial vascular layer and are observed ahead of the endogenous developing vascular network when injected at postnatal day 2 (P2). As the endogenous vasculature reaches the periphery of the retina, where the Lin⁻HSCs have targeted, the cells are incorporated into new blood vessels, forming functional mosaic vessels with mixed populations of injected Lin⁻HSCs and endogenous endothelial cells. In addition, Lin⁻HSCs target the regions of deep and intermediate vascular layers of the retina before vascularization of these layers by endogenous endothelial cells had occurs. Incorporation of Lin⁻HSCs rescues the deep vasculature of rd/rd mice about 2 to about 3 fold over normal and control Lin⁺HSC injected mice. In addition, rescue of the deep vasculature prevents degradation of photoreceptors in the outer nuclear layer of the retina. However, as there is no evidence to suggest that these stem cells can undergo differentiation into retinal neurons or glial cells, the mechanism of neuronal protection remains unknown.

The targeting of Lin⁻HSCs to the astrocytes and deep vascular regions ahead of natural developmental vascularization suggests that the Lin⁻HSCs express cell-surface molecules that function in targeting, similar to targeting of the endogenous endothelial cells during development. R-cadherin adhesion plays an important role in endothelial cell targeting to astrocytes and vascular plexuses during developmental retinal angiogenesis.

R-cadherin has been identified and sequenced in a number of mammals. FIG. 2 depicts the amino acid sequence (SEQ ID NO: 1) of a human variant of R-cadherin preproprotein reported by Kitagawa et al. in the SWISS-PROT database as Accession No. NP 001785, version NP 001785.2, GI:14589893, the relevant disclosure of which is incorporated herein by reference. SEQ ID NO: 1 includes the amino acid sequence IDSMSGR (SEQ ID NO: 2) at positions 222-228.

FIG. 3 depicts the amino acid sequence (SEQ ID NO: 3) of another human variant of R-cadherin preproprotein reported by Tanihara et al. in the SWISS-PROT database as Accession No. P55283, version P55283, GI:1705542, the relevant disclosure of which is incorporated herein by reference. SEQ ID NO: 3 includes the amino acid sequence INSMSGR (SEQ ID NO: 4) at positions 222-228.

FIG. 4 depicts the amino acid sequence (SEQ ID NO: 5) of a murine (mus musculus) variant of R-cadherin preproprotein reported by Hutton et al. in the SWISS-PROT database as Accession No. NP 033997, version NP 033997.1, GI:6753376, the relevant disclosure of which is incorporated herein by reference. SEQ ID NO: 5 includes the amino acid sequence IDSMSGR (SEQ ID NO: 2) at positions 219-225.

Non-selective peptide antagonists of cadherins including the amino acid sequence His-Ala-Val (HAV) have been reported by Blaschuk et al. in U.S. Pat. No. 6,465,427, U.S. Pat. No. 6,3456,512, U.S. Pat. No. 6,169,071, and U.S. Pat. No. 6,031,072. Blaschuk et al. have reported both linear and cyclic peptide antagonists of cadherins, all of which are capable of antagonizing a number of types of cadherin molecules indiscriminately.

Selective peptide antagonists of N-cadherin, which comprise the amino acid sequence Ile-Asn-Pro (INP) have been reported by Williams et al., *Mol. Cell Neurosci.*, 2000;15(5): 456-64. While HAV peptides are non-specific cadherin antagonists, the INP peptide antagonists reported by Williams et al. are specific for N-cadherin and do not exhibit significant binding to other cadherin molecules such as R-cadherin.

Because of the differential distribution of cell adhesion molecules in various tissues in the body, there is an ongoing need for antagonists that are highly selective for specific cell adhesion molecules, in particular for antagonists that are selective for R-cadherin. The selective R-cadherin antagonist peptides of the present invention fulfill this need.

SUMMARY OF THE INVENTION

An isolated peptide useful as a selective antagonist of mammalian R-cadherin comprises 3 to 30 amino acid residues, three contiguous residues of the peptide having the amino acid sequence Ile-Xaa-Ser (IXS); wherein Xaa is an amino acid residue selected from the group consisting of Asp, Asn, Glu, and Gln. Preferably Xaa is Asp or Asn. In one preferred embodiment the peptide comprises at least seven amino acid residues and seven contiguous amino acid residues of the peptide have the amino acid sequence Ile-Xaa-Ser-Met-Ser-Gly-Arg (SEQ ID NO: 6), with Xaa being the same as defined above. The present invention also provides pharmaceutical compositions comprising the R-cadherin antagonist peptides in a pharmaceutically acceptable carrier.

In another preferred embodiment the peptide is a cyclic peptide having 3 to 10 amino acid residues arranged in a ring, three contiguous residues of the peptide having the amino acid sequence Ile-Xaa-Ser; wherein Xaa is an amino acid residue selected from the group consisting of Asp, Asn, Glu, and Gln. Preferably Xaa is Asp or Asn.

A preferred cyclic peptide has the formula:

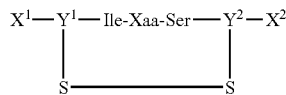

wherein $X^1$ and $X^2$ are independently an amino acid residue or a plurality of up to 10 amino acid residues linked by peptide bonds; $Y^1$ and $Y^2$ are independently amino acid residues linked to one another by a disulfide bond and Xaa is an amino acid residue selected from the group consisting of Asp, Asn, Glu, and Gln.

A particularly preferred cyclic peptide has the amino acid sequence cyclic Cys-Ile-Xaa-Ser-Cys (SEQ ID NO: 7); wherein Xaa is an amino acid residue selected from the group consisting of Asp, Asn, Glu, and Gln, and the peptide ring is formed by a disulfide linkage between the two cysteine residues.

A method of inhibiting R-cadherin mediated cellular adhesion involves contacting R-cadherin expressing cells with an adhesion inhibiting amount of a selective R-cadherin antagonist peptide of the present invention. For example, retinal angiogenesis is inhibited by administering to a patient suffering from abnormal retinal vascular angiogenesis an angiogenesis inhibiting amount of a R-cadherin antagonist peptide of the present invention. Similarly, targeting of lineage negative hematopoietic stem cells to developing vasculature is inhibited by contacting the stem cells with a vasculature targeting inhibiting amount of a R-cadherin antagonist peptide of the present invention. Inhibiting targeting of Lin⁻ HSCs, such as endothelial precursor cells, to developing vasculature is useful for treating diseases associated with abnormal vascular development such as age related macular degeneration and diabetic retinopathy.

BRIEF DESCRIPTION OF THE DRAWINGS

In the Drawings.

FIG. 2 depicts the amino acid sequence of a human variant of R-cadherin preproprotein (SEQ ID NO: 1), which includes the sequence IDSMSGR (SEQ ID NO: 2) at residues 222-228;

FIG. 3 depicts the amino acid sequence of a human variant of R-cadherin preproprotein (SEQ ID NO: 3), which includes the sequence INSMSGR (SEQ ID NO: 4) at residues 222-228;

FIG. 4 depicts the amino acid sequence of a murine variant of R-cadherin preproprotein (SEQ ID NO: 5), which includes the sequence IDSMSGR (SEQ ID NO: 2) at residues 229-225;

FIG. 5(A) illustrates the sequence homology within residues 24-92 of murine N-cadherin and various R-cadherins; note homologies between mammalian R-cadherins from human, mouse and rat, all of which comprise a sequence IDS or INS at residues 53-55, in contrast to chicken R-cadherin and mouse N-cadherin, which have the sequence IDP and INP, respectively at residues 53-55; (B) cyclic and linear peptides corresponding to residues within this region of murine and human R-cadherin and murine N-cadherin were synthesized along with the corresponding control peptides: cyclic CIDSC (SEQ ID NO: 8), cyclic CINPC (SEQ ID NO: 9), IDSMSGR (SEQ ID NO: 2), IDSASGR (SEQ ID NO: 10), INPASGQ (SEQ ID NO: 11), cyclic CSDIC (SEQ ID NO: 12), and cyclic CRADC (SEQ ID NO: 13); the partial cadherin sequences listed in FIG. 5(A) are, from top to bottom, murine N-cadherin (SEQ ID NO: 14), murine R-cadherin (SEQ ID NO: 15), rat R-cadherin (SEQ ID NO: 16), a human R-cadherin (SEQ ID NO: 17), another human R-cadherin (SEQ ID NO: 18), and chicken (gallus gallus) R-cadherin (SEQ ID NO: 19);

DETAILED DESCRIPTION OF PREFERRED EMBODIMENTS

Figure 1:
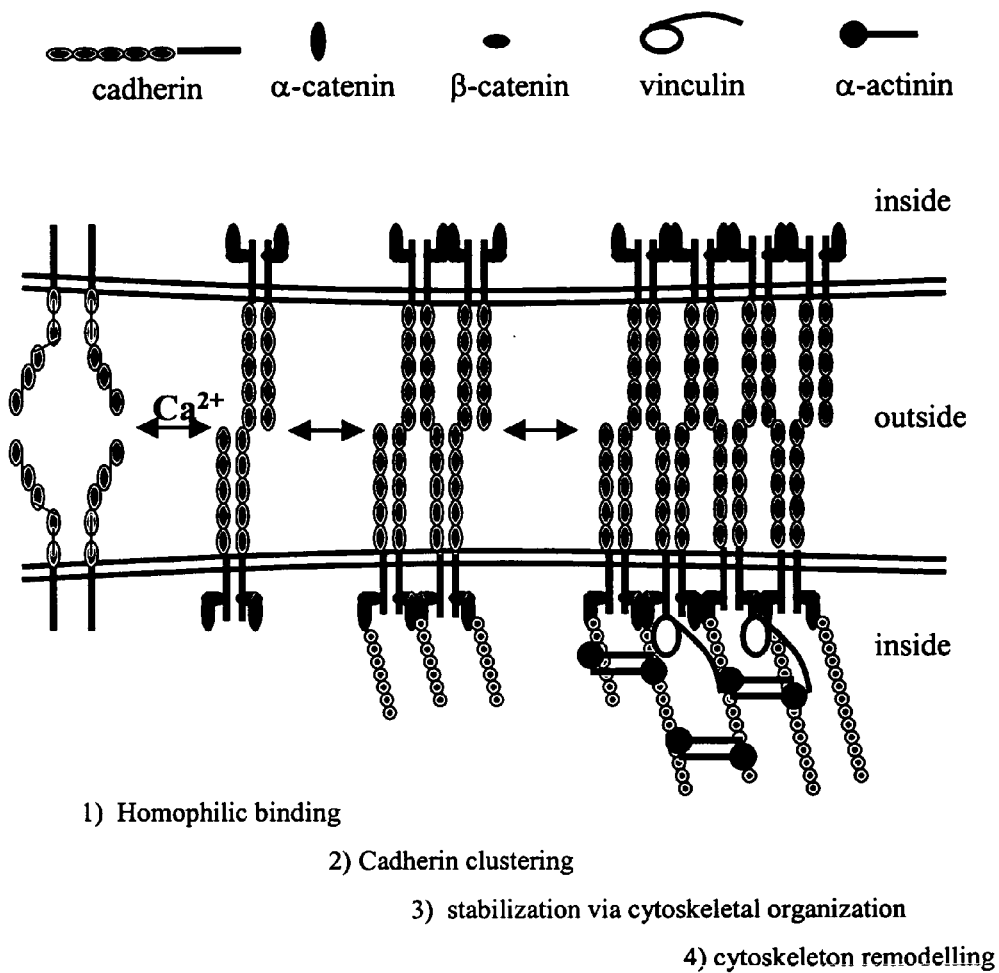
FIG. 1 is a schematic representation of cadherin clustering and cadherin modulated cellular adhesion.

As used herein and in the appended claims, the term "cyclic peptide" refers to molecules comprising a plurality of amino acids linked together in a chain by peptide linkages, the ends of the chain being joined together to form a ring of amino acid residues. The cyclic peptide can be joined together by a peptide bond, a disulfide linkage between two amino acid residues such as cysteine residues, or by any other suitable linking group. Nonpeptidal linking groups can be any chemical moiety that can react with functional groups at each end of the peptide chain to form a link therebetween. For example, two ends of a peptide chain can be linked together by a nonprotein amino acid such as 3-aminobutyric acid or by a disulfide formed from nonpeptidal thiol groups such as a thioglycolic amide at the amino terminal end and amide formed from 2-aminoethane thiol at the carboxy terminal end, for example.

As used herein and in the appended claims, the term "pharmaceutically acceptable" and grammatical variations thereof, in reference to carriers and other excipients, means that the materials are capable of administration to a human patient without the production of undesirable physiological side effects such as retinal or ocular irritation, nausea, dizziness, blurred or impaired vision, cytotoxicity, and the like.

The term "amino acid" as used herein and in the appended claims refers generally to any alpha amino acid. Preferably, the peptides of the present invention comprise the 21 amino acids encoded by the genetic code, although modified amino acid residues can also be included. The amino acids can be in the L, D, or D,L form. Preferably, the peptides of the present invention comprise L-form amino acids. To minimize the likelihood of proteinase degradation in vivo, the administered peptides of the present invention can include one or more D-form amino acid residues.

An isolated peptide, which is a selective antagonist of mammalian R-cadherin comprises 3 to 30 amino acid residues, three contiguous residues of the peptide having the amino acid sequence Ile-Xaa-Ser. Xaa is an amino acid residue selected from the group consisting of Asp, Asn, Glu, and Gln. Preferably Xaa is Asp or Asn. The R-cadherin antagonist peptide of the present invention can be linear or cyclic.

The selective R-cadherin antagonist peptides of the present invention mimic the Ile-Asp-Ser and Ile-Asn-Ser sequences found in the EC1 domain of mammalian R-cadherin, but not in other cadherin molecules. Peptides comprising the Ile-Xaa-Ser sequence can bind to and antagonize mammalian R-cadherin molecules. Xaa preferably is an aspartic acid residue (Asp) or an asparagine residue (Asn), to match the naturally occurring sequences in mammalian R-cadherin molecules. Glutamic acid (Glu) and glutamine (Gln) residues are also suitable for Xaa, due to their chemical similarity to Asp and Asn, respectively.

In one preferred embodiment, the peptide comprises at least seven amino acid residues and seven contiguous amino acid residues of the peptide have the amino acid sequence Ile-Xaa-Ser-Met-Ser-Gly-Arg (SEQ ID NO: 6). Xaa is an amino acid residue selected from the group consisting of Asp, Asn, Glu, and Gln. Preferably Xaa is Asp or Asn.

In another preferred embodiment the peptide is a cyclic peptide having 3 to 10 amino acid residues arranged in a ring, three contiguous residues of the peptide having the amino acid sequence Ile-Xaa-Ser; wherein Xaa is an amino acid residue selected from the group consisting of Asp, Asn, Glu, and Gln, as described above. Preferably Xaa is Asp or Asn.

A preferred cyclic peptide having five amino acids arranged in a ring has the formula:

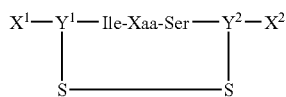

wherein $X^1$ and $X^2$ are independently an amino acid residue or a plurality of up to 10 amino acid residues linked by peptide bonds; $Y^1$ and $Y^2$ are independently amino acid residues linked to one another by a disulfide bond and Xaa is an amino acid residue selected from the group consisting of Asp, Asn, Glu, and Gln. Preferably $Y^1$ and $Y^2$ are both cysteine residues linked together by a disulfide bond (i.e., a cystine residue).

A particularly preferred cyclic peptide has the amino acid sequence cyclo Cys-Ile-Xaa-Ser-Cys (SEQ ID NO: 7); wherein Xaa is an amino acid residue selected from the group consisting of Asp, Asn, Glu, and Gln, and the ring is formed by a disulfide linkage between the two cysteine residues. Preferably Xaa is Asp or Asn.

A method of inhibiting R-cadherin mediated cellular adhesion involves contacting R-cadherin expressing cells with an adhesion inhibiting amount of a R-cadherin antagonist peptide of the present invention. The cells can be contacted in vivo with the peptide antagonist by administering a cellular adhesion inhibiting amount of the antagonist to a mammal suffering from a disease or condition that is treatable by inhibiting R-cadherin mediated cellular adhesion (e.g., retinal diseases characterized by abnormal vascular proliferation). For example, a human patient suffering from age related macular degeneration or diabetic retinopathy can be beneficially treated with a selective R-cadherin antagonist peptide of the present invention. Preferably the antagonist is administered as a pharmaceutical composition comprising the antagonist and a pharmaceutically acceptable carrier therefor.

For the selective targeting or antagonism of R-cadherin the peptides and compositions of the present invention may be administered in a therapeutically effective amount parenterally, orally, by inhalation, or topically in unit dosage form together with pharmaceutically acceptable carriers, vehicles, and adjuvants. The term "parenteral," as used herein, includes intravenous, subcutaneous, intramuscular, intrasternal, intraocular (e.g. intravitreal), and intraperitoneal administration, as well as administration by infusion techniques.

Any suitable route of administration can be utilized, and the pharmaceutical composition including a selective R-cadherin antagonist peptide of the present invention is administered in a dose effective for the intended treatment. Therapeutically effective amounts required to treat a particular medical condition, or inhibit the progress thereof, are readily determined by those skilled in the art using preclinical and clinical studies known in the medical arts.

The term "therapeutically effective amount," as used herein, refers to that amount of active ingredient that elicits the biological or medical response of a tissue, system, animal or human, sought by a clinician or a researcher.

The term "inhibit," as used herein, refers to a slowing, interruption, or stoppage of the medical condition or a biochemical interaction, but does not necessarily indicate a total elimination of the condition or complete interruption of the interaction. A prolonged survivability of a patient or prolonged reduction in the severity of symptoms, in and of itself, indicates that the medical condition is beneficially controlled (i.e., inhibited).

The dosage regimens for the present R-cadherin antagonist peptides and compositions containing the same, are based on several factors such as the age, weight, sex, and type of medical condition of the patient, the severity of the condition, the route of administration, and the antagonist activity of the particular peptide antagonist employed. The dosage regimen may vary depending upon the aforementioned factors. Dosage levels on the order of about 0.01 milligram to about 1000 milligrams per kilogram of body weight are useful for inhibiting retinal angiogenesis, for example. Preferred dosage levels are in the range of about 0.01 milligram to about 100 milligrams per kilogram of body weight.

For administration by injection, a peptide-containing composition embodying the present invention is formulated with a pharmaceutically acceptable carrier such as water, saline, or an aqueous dextrose solution. For injection, a typical daily dose is about 0.01 milligram to about 100 milligrams per kilogram of body weight, injected daily as a single dose or as multiple doses depending upon the aforementioned factors.

Pharmaceutical compositions of the present invention comprising a selective R-cadherin antagonist peptide of the invention and a pharmaceutically acceptable carrier can also include pharmaceutically acceptable excipients. Pharmaceutically acceptable excipients that can be included in the pharmaceutical compositions of the present invention include, for example, physiologically tolerable surfactants, solvents, buffering agents, preservatives, and the like, which are well known in the art.

To inhibit retinal angiogenesis, for example, a patient suffering from abnormal retinal vascular proliferation is administered a therapeutically effective amount of a R-cadherin antagonist peptide of the present invention. The administered peptide selectively binds to R-cadherin in the retina, thus disrupting and inhibiting angiogenesis therein. Preferably the peptide antagonist is administered by intravitreal injection.

Targeting of Lin⁻HSCs to developing vasculature is inhibited by contacting the stem cells with a vasculature targeting inhibiting amount of a selective R-cadherin antagonist peptide of the present invention. Inhibiting targeting of Lin⁻HSCs, such as endothelial precursor cells, to developing vasculature is useful for treating diseases associated with abnormal vascular development such as age related macular degeneration and diabetic retinopathy. Preferably the Lin⁻HSCs are contacted in vivo by administering the present R-cadherin antagonist peptides to a mammal, such as a human, suffering from a vascular proliferative disease or condition.

The following non-limiting examples are provided to further illustrate the various aspects of the invention. One of skill in the art will recognize that modifications of the examples and illustrated embodiments disclosed herein can be made without departure from the spirit and scope of the invention.

EXAMPLE 1

Peptide Synthesis

The peptides of the present invention and various control peptides were synthesized by The Scripps Research Institute Protein and Nucleic Acids core facility using the solid phase synthesis method, and were purified to the highest grade possible (>95% pure) as analyzed by HPLC analysis. The sequences of the peptides were analyzed by mass spectrometry to ensure synthesis of the correct peptides. All peptides were amide blocked at the amino terminus and acetylated at the carboxy terminus. The cyclic peptides were prepared with cysteine residues at the amino and carboxy terminal ends to create a disulfide tether and form a ring containing five amino acid residues. FIG. 5 (B) illustrates the peptides prepared: cylic CIDSC (SEQ ID NO: 9), cylic CINPC (SEQ ID NO: 9), IDSMSGR (SEQ ID NO: 2), IDSASGR (SEQ ID NO: 10), INPASGO (SEQ ID NO: 11), cylic CSDIC (SEQ ID NO: 12), and cylic CRADC (SEQ ID NO: 13).

EXAMPLE 2

L-Cell Transfections

Figure 6:
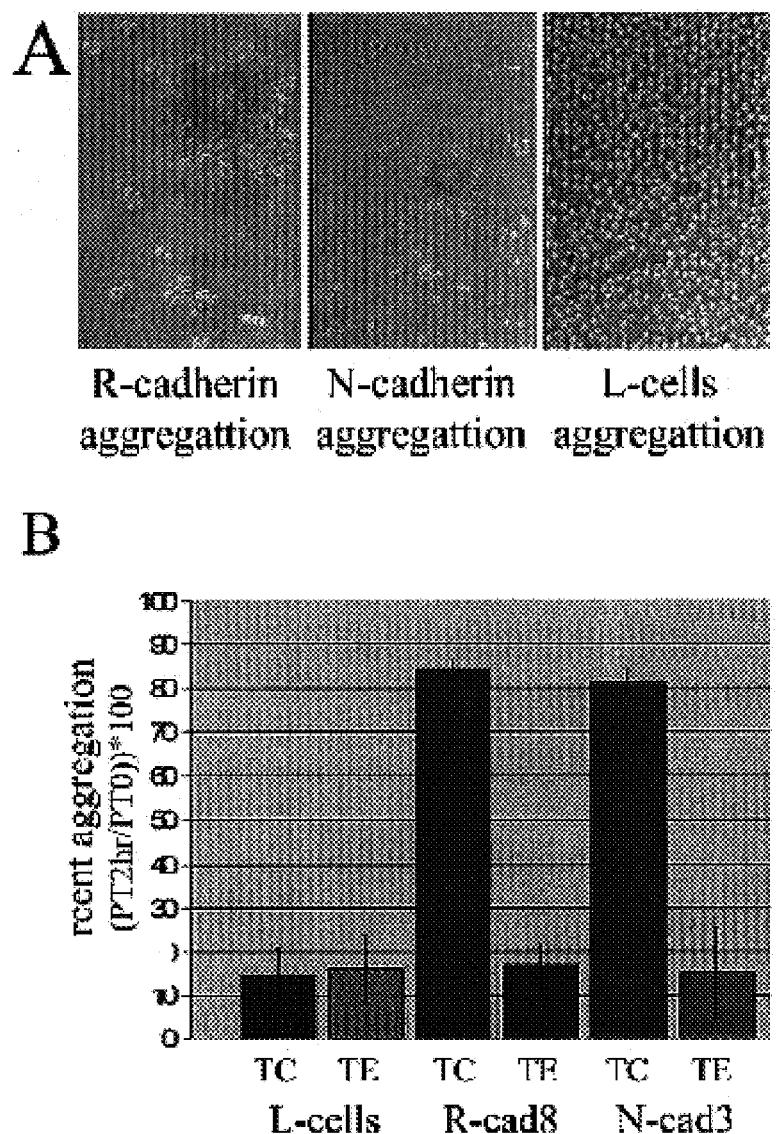
FIG. 6(A) depicts photomicrographs demonstrating aggregation of L-cells expressing R-cadherin and N-cadherin; (B) is a bar graph of percent aggregation of L-cells mediated by R and N-cadherins in the presence and absence of calcium.

Mouse R-cadherin and N-cadherin plasmids were generous gifts from Dr. Masatoshi Takeichi (Kyoto University, Japan). The plasmids were sub-cloned into pDsRed2 N1 vectors (Clontech) to encode for fusion proteins with Red Fluorescent Protein (RFP) attached to the C-terminal end of the cadherin molecules. L-cells (mouse fibroblast L929 cells, ATCC #CRL-2148) were stably transfected with either R or N-cadherin pDsRed2 N1 using the Calcium Phosphate Transfection System (Life Technologies) according to the manufacturer's protocol. After screening by growth in media supplemented with Geneticin (700 μg/mL G418 Geneticin, Gibco BRL), positive clones were selected. Cells were examined for expression of RFP, and were tested for cadherin expression by immunoblotting and immunofluorescence staining. FIG. 6 illustrates the aggregation of L-cells expressing R and N-cadherins. FIG. 6(A) shows photomicrographs of R-cadherin (left) and N-cadherin (middle) expressing L-cells aggregating in calcium containing media, compared to non-transfected L-cells, which did not aggregate. FIG. 6(B) is a bar graph illustrating the percentage of aggregation of the cells shown in FIG. 6(A). N-cadherin and R-cadherin transfected cells trypsinized in a buffer containing about 5 mM calcium chloride (labeled TC) formed large cell clusters, whereas endogenous L-cells showed little aggregation in the calcium containing buffer. Cells that were trypsinized with EDTA in a calcium free buffer (labeled TE) showed little aggregation, regardless of whether the cells were transfected with cadherins or not.

EXAMPLE 3

Cell Culture and Immunofuorescence

Transfected or wild type L-cells were grown in Modified Eagles Medium (MEM) supplemented with Earl's Basic Salt Solution, 2 mM Glutamax, 1 mM sodium pyruvate, 0.1 mM non-essential amino acids, and 10% fetal bovine serum. Transfected cell lines were grown in media supplemented with about 700 μg/mL G418 (all media reagents were from Gibco BRL). For immunofluorescence, the cells were grown to about 75% confluency on glass cover slips. The cells were fixed in 4% paraformaldehyde for about one-half hour followed by blocking with 5% normal goat serum and 5% fetal bovine serum in 1× phosphate buffered saline (PBS). Goat polyclonal antibodies against R-cadherin or N-cadherin (Santa Cruz) were used at 1:200 dilution, and fluorescence was conferred by incubation with Alexa488 labeled anti-goat IgG secondaries (Molecular Probes). Images were created using a Radiance 200 fluorescence confocal microscope (BioRad). For immunoblot analysis, cells were lysed in buffer containing 1% Triton X-100. About 50 μg of total cell lysate was added to each lane of an 8% polyacrylamide gel and proteins separated by electrophoresis. Monoclonal antibodies (1:1000, BD Biosciences) specific for N-cadherin or R-cadherin were used to visualize the corresponding bands.

FIG. 7(A) shows an immunoblot of native L-cells and L-cells transfected with R-cadherin and N-cadherin and stained with R-cadherin antibody. Only the R-cadherin transfected cells exhibited significant levels of R-cadherin expression. FIG. 7(B) shows an immunoblot of native L-cells and L-cells transfected with R-cadherin and N-cadherin and stained with N-cadherin antibody. Only the N-cadherin transfected cells exhibited significant levels of N-cadherin expression. FIG. 7(C) is a fluorescence photomicrograph of R-cadherin expressing cells labeled with fluorescent cadherin antibodies, demonstrating cell surface expression of only the R-cadherin molecules. FIG. 7(D) is a fluorescence photomicrograph of N-cadherin expressing cells labeled with fluorescent cadherin antibodies, demonstrating cell surface expression of only the N-cadherin molecules. FIG. 7(E) is a fluorescence photomicrograph of native L-cells exposed to fluorescent cadherin antibodies, but showing no cell surface expression of cadherin molecules of either type.

EXAMPLE 4

Aggregation Assay

Figure 8:
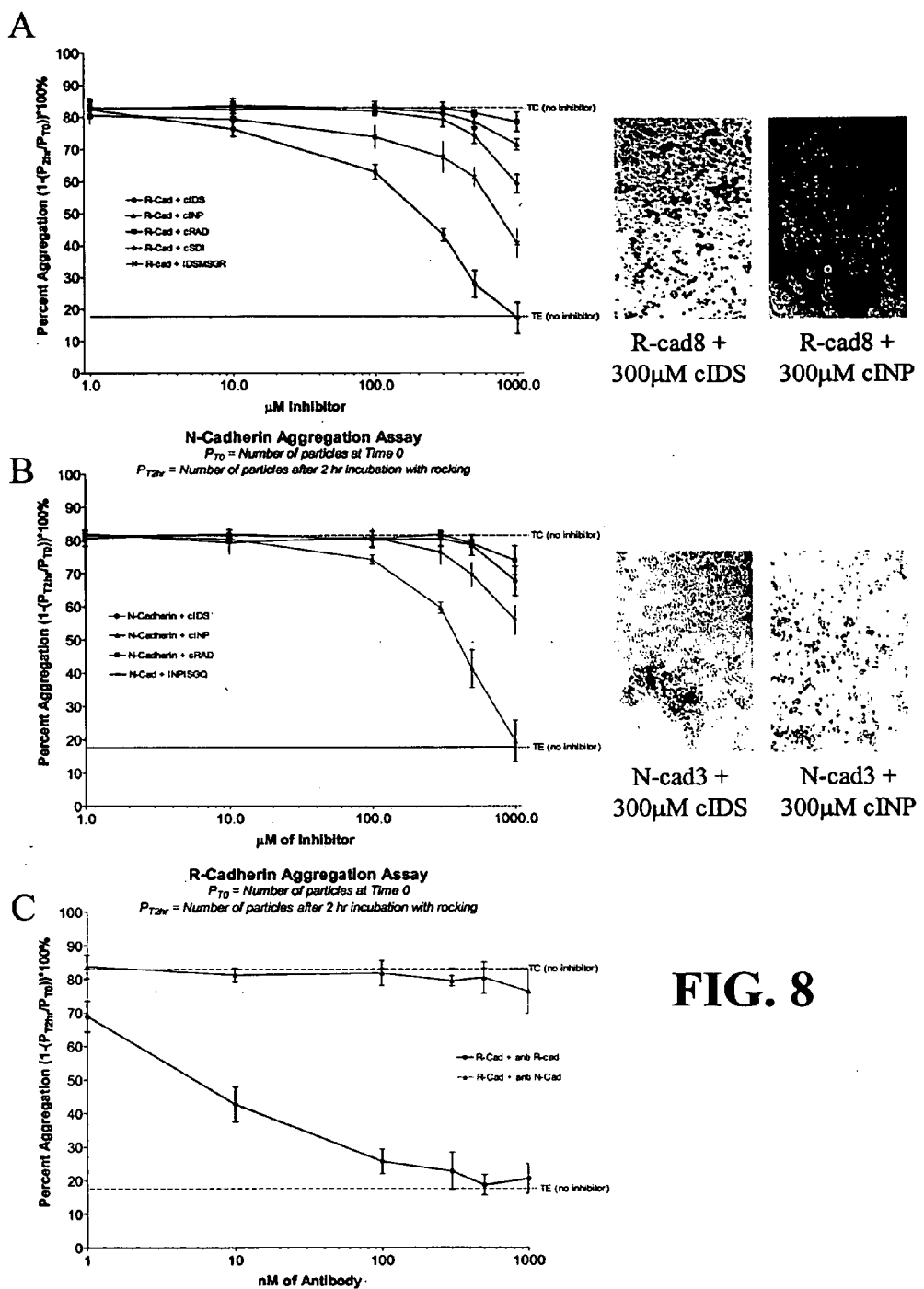
FIG. 8 graphically illustrates selective inhibition of aggregation of cadherin expressing L-cells by IDS containing peptides, which bind to R-cadherin expressing cells, compared with INP containing peptides, which bind to N-cadherin expressing cells.

L-Cells were grown to near confluency followed by trypsinization with 0.01% trypsin +5mM $CaCl_2$ and no EDTA (TC) or 0.01% trypsin with 0.1 mM EDTA and no calcium (TE). The cells were collected and washed, followed by resuspension in Hanks buffer solution (HBSS) +1% BSA with (TC) or without (TE) 5mM $CaCl_2$. Cells were incubated at 37° C. in 0.5 mL solution at $2 \times 10^5$ cells per well of a 24 well plate with rocking at about 60-70 rpm with varying peptide concentrations. All assays were performed in triplicate. The extent of cellular aggregation was represented by the ratio of the total particle number after 2 hours of incubation ($N_{2hr}$) to the initial particle number ($N_0$). Particles were counted on a hemocytometer using the sum of 8 separate 20 μL counts/well, before ($N_0$) and after ($N_t$) incubation. The results are illustrated in FIG. 8.

EXAMPLE 5

Treatment of Mice by Intravitreal Injection of Peptides

Peptides were dissolved in PBS +10% DMSO to a concentration of 10 mM. About 0.5 μL or 1.0 μL of 10 mM peptide solution was injected into the vitreal cavity of 2 day or 7 day-old mice respectively. At P5 or P11, the retinas were dissected as described and the vessels and astrocytes visualized by immunohistochemistry. Quantification of peripheral vascularization, vascular length, and vascular area during superficial vascular formation was achieved by imaging injected retinas under the same microscopy settings. Numbers were then generated using LASERPIX® software (Bio-Rad) with non-injected control littermates used for baseline normalization of the extent of retinal vascularization. Quantification of the effect on deep vascular formation was achieved by focusing anterior to the normal deep vascular plexus using confocal microscopy, and counting the numbers of vessels that had migrated into the photoreceptor layer. The results are presented in FIG. 9.

EXAMPLE 6

Stem Cell Isolation and Enrichment

Bone-marrow cells were isolated from adult transgenic mice in which enhanced GFP was fused to the p-actin promoter (ACTbEGFP, the Jackson Laboratory, Bar Harbor, Me.). Monocytes were then collected by density gradient separation using Histopaque (Sigma) and labeled with biotin-conjugated lineage panel antibodies (CD45, CD3, Ly-6G, CD11, TER-119, Pharmingen, San Diego, Calif.) for Lin⁻ selection. Lin⁺ and Lin⁻ cells were separated using a magnetic separation column (MACS, Miltenyi Biotech, Auborn, Calif.). Since it was determined that CD31⁻ cells represent a better control of a non-functional subpopulation of HSCs as determined by vascular targeting, CD31⁻ cells were isolated from the monocytes by MACS sorting using CD31 antibodies and used as a negative control for the functional Lin⁻HSCs. HSCs from wild type mice were analyzed for the expression of R-cadherin by labeling cells with anti-R-cadherin antibodies (sc-6456, Santa Cruz Biotech) and Alexa-488 labeled donkey anti-goat secondaries (Molecular Probes), and using a FACS calibur (Beckton Dickinson, Franklin Lakes, N.J.) flow cytometer. The results are presented in FIG. 10.

EXAMPLE 7

HSC Cell Incubations, Injections, and Quantification

Figure 11:
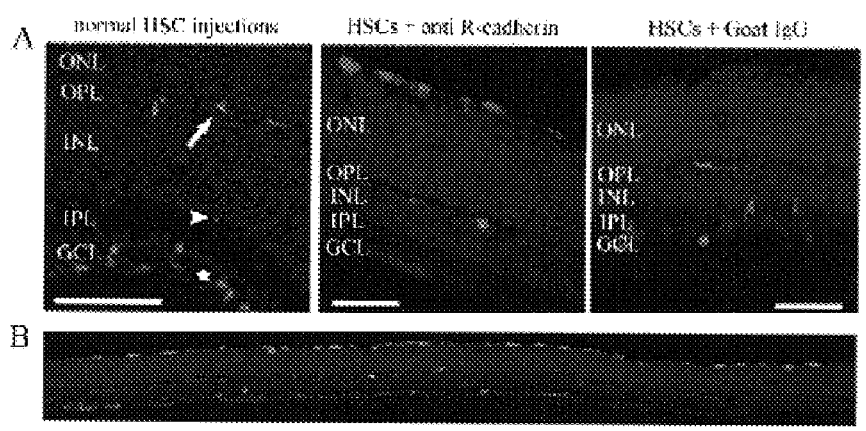
FIG. 11 depicts cross-sectional photomicrographs of rd/rd mouse retinas treated with various peptides of the invention and control peptides.
Figure 12:
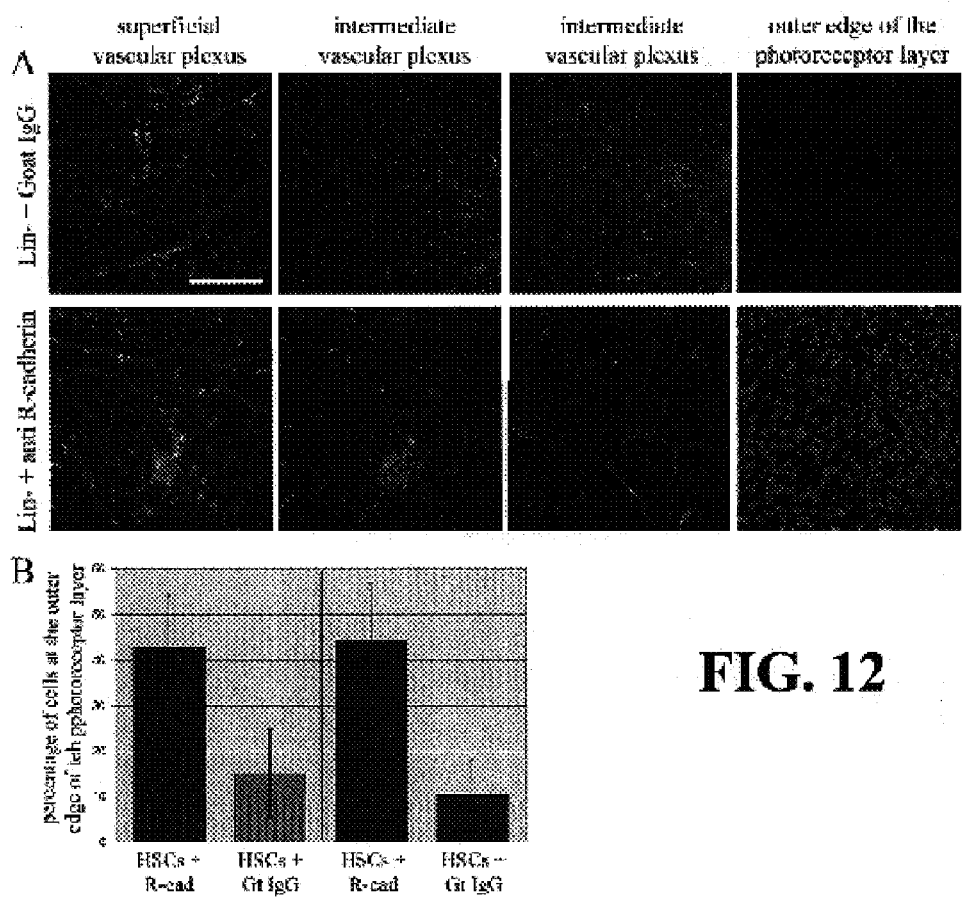
FIG. 12 illustrates the blocking of Lin⁻HSC targeting of developing retinal vasculature by the R-cadherin antagonist peptides of the invention.

Lin⁻HSCs were incubated with 100 nM of R-cadherin blocking antibody (SC-6456, Santa Cruz Biotech), or pre-immune goat IgG in phosphate buffered saline solution for about 1 hour at about 37° C. prior to injection. Intravitreal injections into P6 eyes were performed using 0.5 µL of HSC solution. Retinas were then examined at P12 by whole mount or sections. Targeting of the Lin⁻HSCs was quantified by counting the total number of stem cells within the retina using eight different fields of view per retina: left, right, top, and bottom quadrants (¾ distance to the retina periphery), two intermediate quadrants (¼-½ distance to the periphery), the injection site, and the optic nerve head region. These cells were characterized by their localization to the superficial, intermediate, or deep layers, or by the lack of targeting (cells that lie at the back of the photoreceptor layer). The number of non-targeted cells within the photoreceptor layer is given as a percentage of the total number of stem cells observed. The results are presented in FIG. 11 and FIG. 12.

Discussion

The selective R-cadherin antagonist peptides of the present invention act as peptide mimetics of key recognition motifs of R-cadherin (i.e, the IDS and INS sequences found in mammalian R-cadherins). Without being bound by theory, the present antagonist peptides likely block the adhesion function of R-cadherin molecules by competitive interaction with the EC1 domains of R-cadherin molecules on cell surfaces. The present antagonist peptides are useful for the study of molecular functions, and for the treatment of cellular adhesion-related diseases, and are generally are more diffusible within a tissue upon in vivo injection than antibody-based antagonists.

Tissue morphogenesis during the development of most tissues, including retinal neural tissue, involves the selective binding of cell-cell adhesion molecules. This binding selectivity allows similarly differentiated cells to organize together, and prevents cell types from invading incorrect tissue structures. However, despite the extensive studies on cadherin properties and function, particularly N- and E-cadherins, a general mechanism accounting for cadherin specificity has not yet emerged. The present R-cadherin antagonist peptides selectively interact with mammalian R-cadherin molecules without significant binding to other cadherin classes. These peptides contain the IDS sequence (or its homologs INS, IES, and IQS), which corresponds to a region within cadherin domain EC1, residues 53-55 of SEQ ID NO: 17 and 18, where important interactions within the adhesion interface are reportedly located based on structural, mutational, and sequence homology analysis.

Without being bound by theory, the IDS motif is thought to make direct contacts with the VDI sequence from an adjacent cadherin molecule at the adhesion interface. Because residues 53-55 of cadherins appear to be required for transdimerization, and because unlike other adhesion-important regions this short sequence of amino acids was not conserved amongst classical cadherin family members, this region acts as a determinant for cadherin specificity. Indeed, cyclic IDS (CIDSC, SEQ ID NO: 8) selectively inhibits R-cadherin mediated cellular aggregation, while the corresponding N-cadherin counterpart, cyclic INP (CINPC, SEQ ID NO: 9) selectively inhibits N-cadherin mediated aggregation. N-cadherin and R-cadherin are the most homologous of the cadherin family members. In fact, although all cadherins, including R and N-cadherin prefer to interact in a homophillic manner, R- and N-cadherin are the only two classical cadherin family members where functional heterodimers have been observed. Thus, it is highly unlikely that cyclic IDS and cyclic INP would have distinct functional properties for N and R-cadherin, but overlapping properties for any other cadherin member. These studies demonstrate that the IXS motif (where X is D, N, E, or Q) (i.e. corresponding to R-cadherin residues 53-55, and homologs thereof), plays an important role in mediating homoassociation of R-cadherin molecules. It is likely, based on the specificity of IXS for R-cadherin and INP for N-cadherin, that correspondingly placed residues in other cadherin family members (e.g., the IER motif of E-cadherin and the IEK motif of P-cadherin) also impart specificity to the other classical cadherins as well.

Previous studies have shown that antibodies against R-cadherin disrupt retinal vascularization in vivo. Vascularization of the superficial plexus likely was disrupted due to the interruption of R-cadherin mediated guidance cues relayed by astrocytes lying ahead of the endothelial cells. R-cadherin expression is also observed in the regions where the deep vascular plexuses are subsequently located, just ahead of vascular invasion. R-cadherin molecules within these regions are thought to guide endothelial cells to the correct vascular plexus, since injection of R-cadherin blocking antibodies causes vessels to bypass the normal vascularized layers.

Similar vascular phenotypes have now been generated by injection of cyclic IDS (CIDSC, SEQ ID NO: 8) during both superficial and deep retinal vascularization. Since cyclic IDS selectively disrupted R-cadherin mediated aggregation to a significant extent in vitro (i.e., without significant disruption of N-cadherin mediated aggregation), it is likely that the in vivo vascular phenotype was generated by high affinity interactions of cyclic IDS with R-cadherin, as well. In addition, injection of cyclic INP (CINPC, SEQ ID NO: 9), which was an effective inhibitor of N-cadherin mediated aggregation but not R-cadherin aggregation in vitro, did not result in a significant retinal vascular phenotype. Together, these results confirm a specific role for R-cadherin during vascular guidance.

The design of the selective R-cadherin antagonist peptides of the present invention was based on structural, biochemical, and mutational analysis of various members of the classical cadherin family. Tryptophan-2 is known to be important for cadherin function along with the HAV sequence at amino acid residues 79-81 of N-cadherin and R-cadherin. In fact, linear and cyclic peptides containing the HAV sequence reportedly block N-cadherin mediated neurite outgrowth in vitro. However, these sequences are absolutely conserved across all cadherin molecules and therefore carinot confer specificity of binding. Other residues must also make important contacts within the dimerization interface, with some non-conserved residues important for cadherin recognition. Attention was focused on residues within the amino terminal cadherin repeat (EC1). The majority of contact-important residues were localized to three regions, amino acids 35-45, amino acids 53-59, and amino acids 79-86. Residues 53-59, contained the majority of these cadherin specific residues potentially important in the formation of the dimerization interface. Of these, residues 53-55 were of particular significance. Thus, peptide mimetics were designed from this region to optimize the probability that R-cadherin specific peptides would be produced. Similar peptides against sequences from mouse N-cadherin, the most closely related cadherin family member, and other control peptides were designed and used for comparative analysis.

Cadherin Mediated Aggregation

Figure 7:
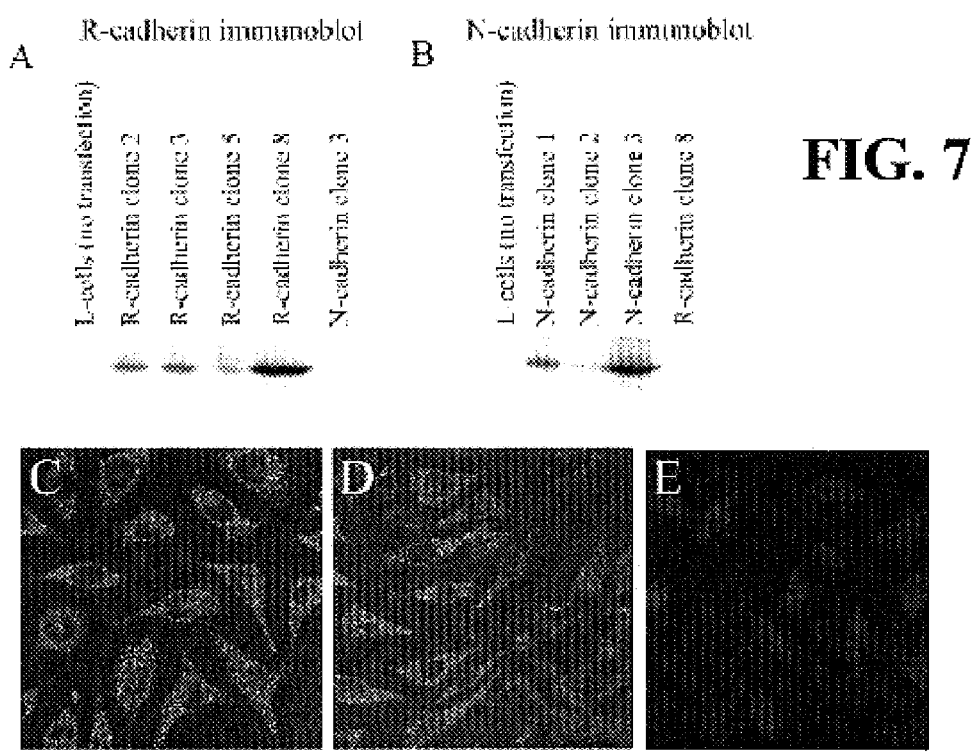
FIG. 7 demonstrates stable transfection of L-cells with R-cadherin and N-cadherin; (A) R-cadherin immunoblot; (B) N-cadherin immunoblot; (C-E) photomicrographs of stained L-cells demonstrating expression of R-cadherin (C), and N-cadherin (D), compared to cells expressing neither R nor N-cadherin (E)

Mouse fibroblast cells (lineage L929), commonly referred to as L-cells, were chosen because they are known to contain no endogenous cadherin expression. R-cadherin stable transfectants were created and used to test the effects of the designed peptides on R-cadherin mediated aggregation. N-cadherin stable transfectants were also created and used to evaluate the peptides for cadherin selectivity, based on their effects on N-cadherin mediated aggregation. Immunoblot analysis detected high levels of R-cadherin and no N-cadherin expression in R-cadherin clone 8 (R-cad8), while high levels of N-cadherin expression and no R-cadherin expression was found in N-cadherin clone 3 (N-cad3), as shown in FIG. 7. Immunofluorescence confirmed the expression of the appropriate cadherin in these chosen clones. When tested in the aggregation assay, the morphology of the transfected cell lines was altered as a result of cadherin transfection. While the parent (i.e., non-transfected) L-cells remained dissociated as single cell particles, the mouse R-cadherin and N-cadherin transfectants formed large, calcium-dependent (TC buffer), cell clusters due to tight intercellular associations, as shown in FIG. 6(A). Cadherin mediated aggregation clusters were eliminated by initial trypsinization of the cells with EDTA solution and aggregation in calcium-free buffer (TE buffer), as shown in FIG. 6(B).

Peptide Effects on Cell Aggregation

Peptides were added at varying concentrations to the aggregation wells to test their effectiveness at blocking cadherin mediated adhesion. Cyclic IDS inhibited R-cadherin mediated aggregation with an $IC_{50}$ of around 300 µM. The linear peptide IDSMSGR (SEQ ID NO: 2), also blocked R-cadherin mediated adhesion. However, its effectiveness ($IC_{50}$~900 µM) was about 3 times lower than that of cyclic IDS. As the cyclic peptides also proved to be much more soluble and easier to work with than the linear peptides, further emphasis was focused solely on analysis of cyclic peptides (FIG. 8(A)). The effects of cyclic IDS were specific for R-cadherin, as little effect on N-cadherin aggregation was observed. In contrast, the corresponding N-cadherin specific sequence, cyclic INP, inhibited N-cadherin mediated aggregation with an $IC_{50}$ just below 300 µM (FIG. 8(B)), similar to the effects of cyclic IDS on R-cadherin aggregation. Cyclic INP had little effect on R-cadherin mediated aggregation.

The other control peptides, cyclic RAD (CRADC, SEQ ID NO: 13) and cyclic SDI (CSDIC, SEQ ID NO: 12) had little effect on either R-cadherin or N-cadherin mediated aggregation. A cyclic HAV peptide (CHAVC, SEQ ID NO: 20), already known to be effective at blocking adhesion mediated by any classical cadherin molecules, was tested as a comparison. In our assay, cyclic HAV blocked R-cadherin and N-cadherin mediated aggregation with $IC_{50S}$ between 150 and 200 µM. Thus, cyclic IDS and cyclic INP selectively blocked R or N cadherin adhesion respectively, with only slightly lower affinities than the non-specific pan cadherin blocking peptide. Previous studies using antibodies against R-cadherin were shown to disrupt normal retina developmental vascularization. These antibodies were also effective at disrupting cadherin mediated aggregation in our assay system with an $IC_{50}$ of around 10 nM, as shown in FIG. 8(C).

Effects of Peptides on Retinal Vascularization

Peptides were injected into the vitreal cavity of postnatal mouse eyes. When cyclic IDS or cyclic HAV peptides were injected into two-day old mouse eyes, and the resulting vasculature was examined three days later at postnatal day 5 (P5), vascular formation was disrupted with results similar to those observed by antibody injections. These retinas were characterized as having less extensive peripheral vascularization, and fewer interconnecting vessels within the vascularized regions compared to normal, non-injected littermate controls. Overall, vascularization of the superficial layer was cut in half by R-cadherin blocking peptides while retinas with N-cadherin specific cyclic INP injections were relatively normal (see FIGS. 9(A-C)).

Figure 9:
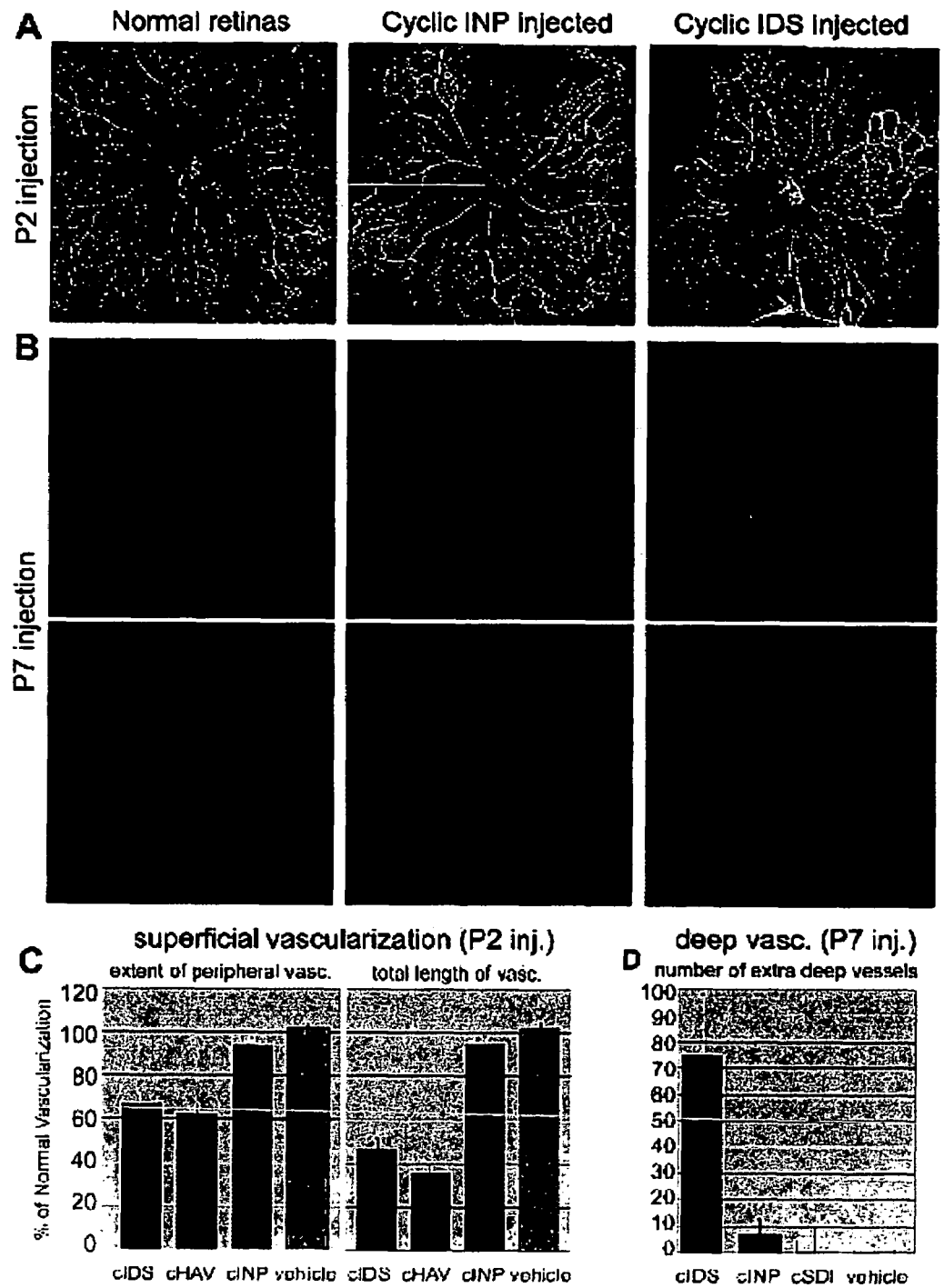
FIG. 9 illustrates selective inhibition of mouse retinal vascularization after intravitreal injection of cyclic CIDSC (SEQ ID NO: 8), compared with cyclic CINPC (SEQ ID NO: 9); (A) depicts photomicrographs of rd/rd mouse retinas at the P2 stage of development; (B) depicts photomicrographs of rd/rd mouse retinas at the P7 stage of development; (C) is a bar graph of superficial vascularization; (D) is a bar graph of deep vascularization.

Selective R-cadherin antagonist peptides of the present invention disrupted normal vascularization of the deep retinal layers as well. When cyclic IDS peptide was injected at P7, just before vessels of the superficial vascular network dive and begin formation of the deep vascular plexus, the resultant P11 vasculature was characterized by numerous vascular sprouts that had migrated past the normal deep vascular plexus and into the avascular photoreceptor layer. Again, this is similar to the effects observed previously when R-cadherin antibodies were injected. In contrast, the deep vascular plexus of eyes injected with cyclic INP peptide formed normally, as shown in FIGS. 9(B and D).

R-Cadherin is Expressed by Lin⁻HSCs

Figure 10:
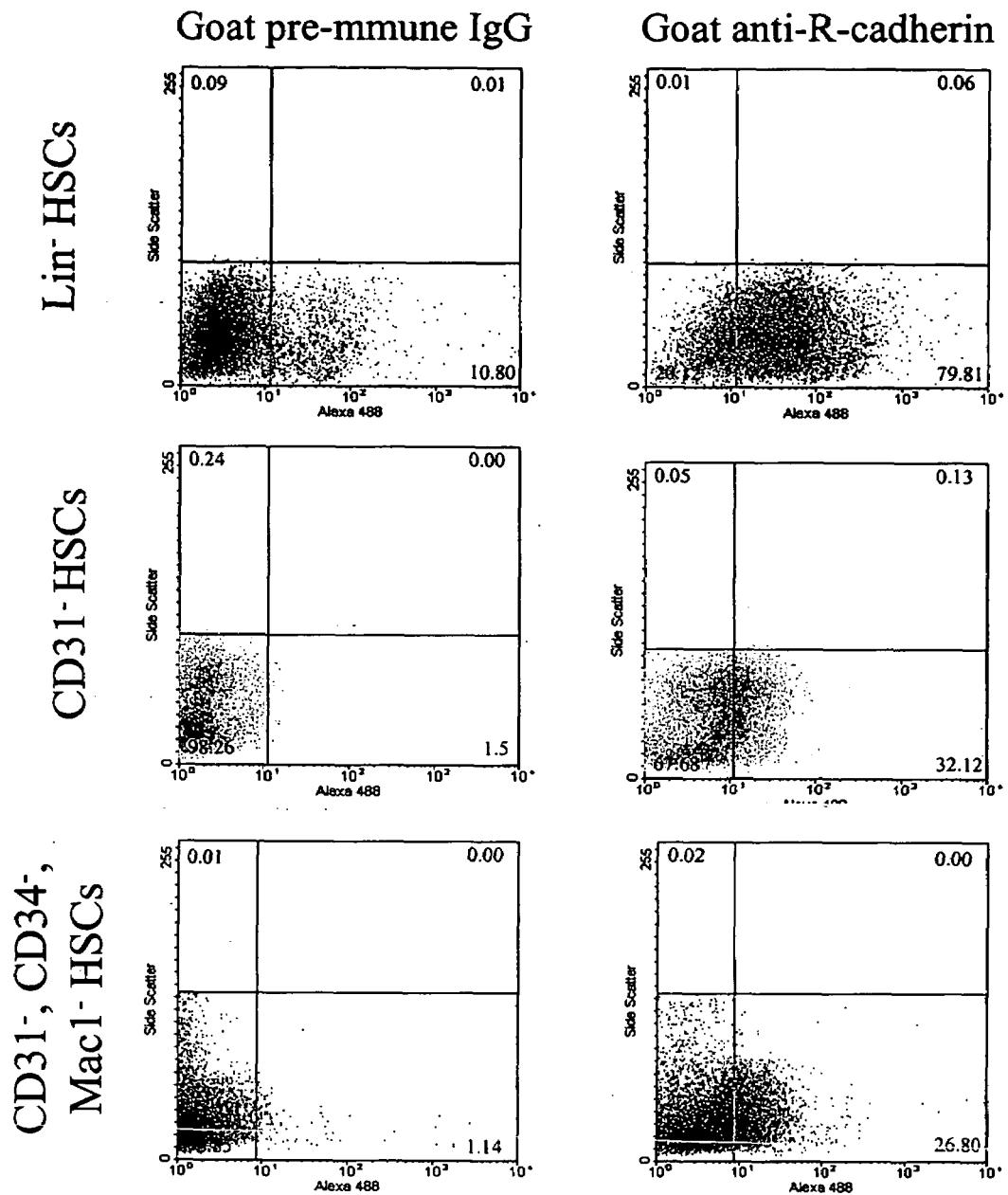
FIG. 10 illustrates the results of flow cytometry analysis of R-cadherin expression in hematopoietic stem cells (HSC)

Hematopoietic stem cell (HSC) expression of R-cadherin was analyzed to determine if R-cadherin cell adhesion molecules were expressed at the cell surface of functionally targeting cells. Using flow cytometry analysis, R-cadherin was expressed at the cell surface of nearly 80% of the Lin⁻ subpopulation of HSCs while only 30% of the Lin⁺ cells express R-cadherin (FIG. 10). Based on the relative fluorescence intensities between the two cell populations, it is likely that the Lin⁻ cells also express higher concentrations of R-cadherin at their cell surface, than the small portion of R-cadherin positive Lin⁺ cells. Thus, the majority of cells within the subpopulation that functionally targets the retinal vasculature express R-cadherin while most of the cells from the non-targeting subpopulation do not. Interestingly, a different subpopulation of HSCs that are CD31, CD34, and Mac1 negative and have no targeting function at all, contained even fewer R-cadherin expressing cells.

R-Cadherin Blocking Antibodies and Peptides Disrupt HSC Targeting

To examine the degree to which R-cadherin cell-cell adhesion functions in targeting of HSCs to the distinct retinal vascular layers, Lin⁻HSCs were blocked with R-cadherin specific, blocking antibodies prior to injection. Six days after injection, normal Lin⁻HSCs are only found localized to the three vascular layers: 1) the superficial vascular plexus localized within the ganglion cell layer, 2) the deep vascular plexus localized near the outer plexiform layer, and 3) the intermediate layer localized at the front edge of the inner nuclear layer. FIG. 11(A) shows cross-sections of retinas after injection of normal Lin⁻HSCs (left), Lin⁻HSCs incubated with adhesion blocking R-cadherin antibodies (middle) and Lin⁻HSCs incubated with pre-immune goat IgG (right).

When the Lin⁻HSCs were pre-incubated with anti-R-cadherin antibodies prior to injection, many of these cells lost their ability to target correctly, while cells pre-incubated with pre-immune IgG function similar to non-blocked HSCs. Targeting to the deep and intermediate vascular layers appears to be especially affected by blocking R-cadherin adhesion as relatively few R-cadherin blocked HSCs were found localized within these regions. The cells localized to the superficial vascular plexus also appeared less organized and were not co-localized with the endogenous vasculature to the same extent as normal Lin⁻HSCs or those pre-incubated with pre-immune IgG.

Many of the Lin⁻HSCs pre-incubated with R-cadherin antibody, migrated through the retina past all three vascular layers, and attached themselves to the outer edge of the photoreceptors near the RPE layer. Almost half of the R-cadherin blocked HSCs were found at the outer edge of the photoreceptor layer (FIG. 11(B)). In comparison, control retinas injected with HSCs pre-incubated with pre-immune IgG only had 15% of the HSCs mistargeted to this region. A large portion of the mistargeted cells from the control reginas were found near the injection site, and can likely be attributed to cells that were released subretinally as the needle was being removed. When the injection site was excluded from the calculation, the number of mistargeted pre-immune IgG incubated HSCs was reduced to 10%. Since almost no Lin⁻HSCs are observed within this "extra deep" layer normally, this small percentage of mistargeted control IgG incubated HSCs can likely be attributed to the fact that the pre-immune IgG was able to bind to about 10% of the Lin⁻cells (FIG. 10). These bound IgG molecules may non-specifically prevent normal adhesion simply due to steric hindrances. However, the difference between the number of mistargeted cells due to specific R-cadherin blocking, and non-specific IgG blocking, is significant.

FIG. 12(A) shows confocal images through z-planes of the three vascular plexuses and the outer edge of the photoreceptor layer. Normal targeting within correct vascular plexuses and along endogenous vessels was observed by Lin⁻HSCs blocked with pre-immune goat IgG. Blocking R-cadherin adhesion caused many Lin⁻HSCs to be localized at the outer edge of the photreceptor layer, and cells targeted to the normal vascular plexuses tended to clump together and were not localized along endogenous vessels. FIG. 12(B) is a bar graph demonstrating that the percentage of mistargeted cells relative to the entire population of HSCs within the retina was significantly greater for the R-cadherin blocked population of Lin⁻HSCs (P values <0.01).

The foregoing description is to be taken as illustrative, but not limiting. Still other variants within the spirit and scope of the present invention will readily present themselves to those skilled in the art.

We claim:

1. An isolated peptide composition consisting of SEQ ID NO: 8.

2. A pharmaceutical for inhibiting retinal angiogenesis comprising the peptide of claim 1 and a pharmaceutically accptable excipient in a pharmaceutically acceptable carrier therefor.

* * * * *

SEQUENCE LISTING

<160> NUMBER OF SEQ ID NOS: 20

<210> SEQ ID NO 1
<211> LENGTH: 916
<212> TYPE: PRT
<213> ORGANISM: HOMO SAPIENS

<400> SEQUENCE: 1

```
Met Thr Ala Gly Ala Gly Val Leu Leu Leu Leu Ser Leu Ser Gly
 1               5                  10                  15

Ala Leu Arg Ala His Asn Glu Asp Leu Thr Thr Arg Glu Thr Cys Lys
            20                  25                  30

Ala Gly Phe Ser Glu Asp Asp Tyr Thr Ala Leu Ile Ser Gln Asn Ile
            35                  40                  45

Leu Glu Gly Glu Lys Leu Leu Gln Val Lys Phe Ser Ser Cys Val Gly
        50                  55                  60

Thr Lys Gly Thr Gln Tyr Glu Thr Asn Ser Met Asp Phe Lys Val Gly
65                  70                  75                  80

Ala Asp Gly Thr Val Phe Ala Thr Arg Glu Leu Gln Val Pro Ser Glu
                85                  90                  95

Gln Val Ala Phe Thr Val Thr Ala Trp Asp Ser Gln Thr Ala Glu Lys
            100                 105                 110

Trp Asp Ala Val Val Arg Leu Leu Val Ala Gln Thr Ser Ser Pro His
            115                 120                 125

Ser Gly His Lys Pro Gln Lys Gly Lys Lys Val Val Ala Leu Asp Pro
        130                 135                 140
```

```
Ser Pro Pro Pro Lys Asp Thr Leu Leu Pro Trp Pro Gln His Gln Asn
145                 150                 155                 160

Ala Asn Gly Leu Arg Arg Lys Arg Asp Trp Val Ile Pro Pro Ile
            165                 170                 175

Asn Val Pro Glu Asn Ser Arg Gly Pro Phe Pro Gln Gln Leu Val Arg
                180                 185                 190

Ile Arg Ser Asp Lys Asp Asn Asp Ile Pro Ile Arg Tyr Ser Ile Thr
            195                 200                 205

Gly Val Gly Ala Asp Gln Pro Pro Met Glu Val Phe Ser Ile Asp Ser
210                 215                 220

Met Ser Gly Arg Met Tyr Val Thr Arg Pro Met Asp Arg Glu Glu His
225                 230                 235                 240

Ala Ser Tyr His Leu Arg Ala His Ala Val Asp Met Asn Gly Asn Lys
            245                 250                 255

Val Glu Asn Pro Ile Asp Leu Tyr Ile Tyr Val Ile Asp Met Asn Asp
                260                 265                 270

Asn Arg Pro Glu Phe Ile Asn Gln Val Tyr Asn Gly Ser Val Asp Glu
            275                 280                 285

Gly Ser Lys Pro Gly Thr Tyr Val Met Thr Val Thr Ala Asn Asp Ala
290                 295                 300

Asp Asp Ser Thr Thr Ala Asn Gly Met Val Arg Tyr Arg Ile Val Thr
305                 310                 315                 320

Gln Thr Pro Gln Ser Pro Ser Gln Asn Met Phe Thr Ile Asn Ser Glu
            325                 330                 335

Thr Gly Asp Ile Val Thr Val Ala Ala Gly Leu Asp Arg Glu Lys Val
                340                 345                 350

Gln Gln Tyr Thr Val Ile Val Gln Ala Thr Asp Met Glu Gly Asn Leu
            355                 360                 365

Asn Tyr Gly Leu Ser Asn Thr Ala Thr Ala Ile Ile Thr Val Thr Asp
370                 375                 380

Val Asn Asp Asn Pro Pro Glu Phe Thr Ala Ser Thr Phe Ala Gly Glu
385                 390                 395                 400

Val Pro Glu Asn Arg Val Glu Thr Val Val Ala Asn Leu Thr Val Met
            405                 410                 415

Asp Arg Asp Gln Pro His Ser Pro Asn Trp Asn Ala Val Tyr Arg Ile
                420                 425                 430

Ile Ser Gly Asp Pro Ser Gly His Phe Ser Val Arg Thr Asp Pro Val
            435                 440                 445

Thr Asn Glu Gly Met Val Thr Val Lys Ala Val Asp Tyr Glu Leu
450                 455                 460

Asn Arg Ala Phe Met Leu Thr Val Met Val Ser Asn Gln Ala Pro Leu
465                 470                 475                 480

Ala Ser Gly Ile Gln Met Ser Phe Gln Ser Thr Ala Gly Val Thr Ile
            485                 490                 495

Ser Ile Met Asp Ile Asn Glu Ala Pro Tyr Phe Pro Ser Asn His Lys
                500                 505                 510

Leu Ile Arg Leu Glu Glu Gly Val Pro Pro Gly Thr Val Leu Thr Thr
            515                 520                 525

Phe Ser Ala Val Asp Pro Asp Arg Phe Met Gln Gln Ala Val Arg Tyr
530                 535                 540

Ser Lys Leu Ser Asp Pro Ala Ser Trp Leu His Ile Asn Ala Thr Asn
545                 550                 555                 560
```

-continued

```
Gly Gln Ile Thr Thr Ala Ala Val Leu Asp Arg Glu Ser Leu Tyr Thr
            565                 570                 575

Lys Asn Asn Val Tyr Glu Ala Thr Phe Leu Ala Ala Asp Asn Gly Ile
            580                 585                 590

Pro Pro Ala Ser Gly Thr Gly Thr Leu Gln Ile Tyr Leu Ile Asp Ile
            595                 600                 605

Asn Asp Asn Ala Pro Glu Leu Leu Pro Lys Glu Ala Gln Ile Cys Glu
            610                 615                 620

Lys Pro Asn Leu Asn Ala Ile Asn Ile Thr Ala Ala Asp Ala Asp Val
625                 630                 635                 640

Asp Pro Asn Ile Gly Pro Tyr Val Phe Glu Leu Pro Phe Val Pro Ala
                645                 650                 655

Ala Val Arg Lys Asn Trp Thr Ile Thr Arg Leu Asn Gly Asp Tyr Ala
                660                 665                 670

Gln Leu Ser Leu Arg Ile Leu Tyr Leu Glu Ala Gly Met Tyr Asp Val
            675                 680                 685

Pro Ile Ile Val Thr Asp Ser Gly Asn Pro Pro Leu Ser Asn Thr Ser
            690                 695                 700

Ile Ile Lys Val Lys Val Cys Pro Cys Asp Asp Asn Gly Asp Cys Thr
705                 710                 715                 720

Thr Ile Gly Ala Val Ala Ala Ala Gly Leu Gly Thr Gly Ala Ile Val
                725                 730                 735

Ala Ile Leu Ile Cys Ile Leu Ile Leu Leu Thr Met Val Leu Leu Phe
                740                 745                 750

Val Met Trp Met Lys Arg Arg Glu Lys Glu Arg His Thr Lys Gln Leu
            755                 760                 765

Leu Ile Asp Pro Glu Asp Val Arg Asp Asn Ile Leu Lys Tyr Asp
            770                 775                 780

Glu Glu Gly Gly Gly Glu Asp Gln Asp Tyr Asp Leu Ser Gln Leu
785                 790                 795                 800

Gln Gln Pro Glu Ala Met Gly His Val Pro Ser Lys Ala Pro Gly Val
                805                 810                 815

Arg Arg Val Asp Glu Arg Pro Val Gly Ala Glu Pro Gln Tyr Pro Ile
                820                 825                 830

Arg Pro Met Val Pro His Pro Gly Asp Ile Gly Asp Phe Ile Asn Glu
                835                 840                 845

Gly Leu Arg Ala Ala Asp Asn Asp Pro Thr Ala Pro Pro Tyr Asp Ser
850                 855                 860

Leu Leu Val Phe Asp Tyr Glu Gly Ser Gly Ser Thr Ala Gly Ser Val
865                 870                 875                 880

Ser Ser Leu Asn Ser Ser Ser Gly Asp Gln Asp Tyr Asp Tyr Leu
                885                 890                 895

Asn Asp Trp Gly Pro Arg Phe Lys Lys Leu Ala Asp Met Tyr Gly Gly
                900                 905                 910

Gly Glu Glu Asp
        915
```

<210> SEQ ID NO 2
<211> LENGTH: 7
<212> TYPE: PRT
<213> ORGANISM: HOMO SAPIENS

<400> SEQUENCE: 2

```
Ile Asp Ser Met Ser Gly Arg
1               5
```

<210> SEQ ID NO 3
<211> LENGTH: 916
<212> TYPE: PRT
<213> ORGANISM: HOMO SAPIENS

<400> SEQUENCE: 3

Met Thr Ala Gly Ala Gly Val Leu Leu Leu Leu Ser Leu Ser Gly
 1               5                  10                  15

Ala Leu Arg Ala His Asn Glu Asp Leu Thr Thr Arg Glu Thr Cys Lys
            20                  25                  30

Ala Gly Phe Ser Glu Asp Asp Tyr Thr Ala Leu Ile Ser Gln Asn Ile
        35                  40                  45

Leu Glu Gly Glu Lys Leu Leu Gln Val Lys Phe Ser Ser Cys Val Gly
    50                  55                  60

Thr Lys Gly Thr Gln Tyr Glu Thr Asn Ser Met Asp Phe Lys Val Gly
65                  70                  75                  80

Ala Asp Gly Thr Val Phe Ala Thr Arg Glu Leu Gln Val Pro Ser Glu
                85                  90                  95

Gln Val Ala Phe Thr Val Thr Ala Trp Asp Ser Gln Thr Ala Glu Lys
            100                 105                 110

Trp Asp Ala Val Val Arg Leu Leu Val Ala Gln Thr Ser Ser Pro His
        115                 120                 125

Ser Gly His Lys Pro Gln Lys Gly Lys Lys Val Val Ala Leu Asp Pro
    130                 135                 140

Ser Pro Pro Lys Asp Thr Leu Leu Pro Trp Pro Gln His Gln Asn
145                 150                 155                 160

Ala Asn Gly Leu Arg Arg Arg Lys Arg Asp Trp Val Ile Pro Pro Ile
                165                 170                 175

Asn Val Pro Glu Asn Ser Arg Gly Pro Phe Pro Gln Gln Leu Val Arg
            180                 185                 190

Ile Arg Ser Asp Lys Asp Asn Asp Ile Pro Ile Arg Tyr Ser Ile Thr
        195                 200                 205

Gly Val Gly Ala Asp Gln Pro Pro Met Glu Val Phe Ser Ile Asn Ser
    210                 215                 220

Met Ser Gly Arg Met Tyr Val Thr Arg Pro Met Asp Arg Glu Glu His
225                 230                 235                 240

Ala Ser Tyr His Leu Arg Ala His Ala Val Asp Met Asn Gly Asn Lys
                245                 250                 255

Val Glu Asn Pro Ile Asp Leu Tyr Ile Tyr Val Ile Asp Met Asn Asp
            260                 265                 270

Asn His Pro Glu Phe Ile Asn Gln Val Tyr Asn Cys Ser Val Asp Glu
        275                 280                 285

Gly Ser Lys Pro Gly Thr Tyr Val Met Thr Ile Thr Ala Asn Asp Ala
    290                 295                 300

Asp Asp Ser Thr Thr Ala Asn Gly Met Val Arg Tyr Arg Ile Val Thr
305                 310                 315                 320

Gln Thr Pro Gln Ser Pro Ser Gln Asn Met Phe Thr Ile Asn Ser Glu
                325                 330                 335

Thr Gly Asp Ile Val Thr Val Ala Ala Gly Trp Asp Arg Glu Lys Val
            340                 345                 350

Gln Gln Tyr Thr Val Ile Val Gln Ala Thr Asp Met Glu Gly Asn Leu
        355                 360                 365

Asn Tyr Gly Leu Ser Asn Thr Ala Thr Ala Ile Ile Thr Val Thr Asp

-continued

```
                370                 375                 380
Val Asn Asp Asn Pro Ser Glu Phe Thr Ala Ser Thr Phe Ala Gly Glu
385                 390                 395                 400

Val Pro Glu Asn Ser Val Glu Thr Val Val Ala Asn Leu Thr Val Met
                405                 410                 415

Asp Arg Asp Gln Pro His Ser Pro Asn Trp Asn Ala Val Tyr Arg Ile
                420                 425                 430

Ile Ser Gly Asp Pro Ser Gly His Phe Ser Val Arg Thr Asp Pro Val
                435                 440                 445

Thr Asn Glu Gly Met Val Thr Val Lys Ala Val Asp Tyr Glu Leu
450                 455                 460

Asn Arg Ala Phe Met Leu Thr Val Met Val Ser Asn Gln Ala Pro Leu
465                 470                 475                 480

Ala Ser Gly Ile Gln Met Ser Phe Gln Ser Thr Ala Gly Val Thr Ile
                485                 490                 495

Ser Ile Met Asp Ile Asn Glu Ala Pro Tyr Phe Pro Ser Asn His Lys
                500                 505                 510

Leu Ile Arg Leu Glu Glu Gly Val Pro Pro Gly Thr Val Leu Thr Thr
                515                 520                 525

Phe Ser Ala Val Asp Pro Asp Arg Phe Met Gln Gln Ala Val Arg Tyr
                530                 535                 540

Ser Lys Leu Ser Asp Pro Ala Ser Trp Leu His Ile Asn Ala Thr Asn
545                 550                 555                 560

Gly Gln Ile Thr Thr Val Ala Val Leu Asp Arg Glu Ser Leu Tyr Thr
                565                 570                 575

Lys Asn Asn Val Tyr Glu Ala Thr Phe Leu Ala Ala Asp Asn Gly Ile
                580                 585                 590

Pro Pro Ala Ser Gly Thr Gly Thr Leu Gln Ile Tyr Leu Ile Asp Ile
                595                 600                 605

Asn Asp Asn Ala Pro Glu Leu Leu Pro Lys Glu Ala Gln Ile Cys Glu
                610                 615                 620

Arg Pro Asn Leu Asn Ala Ile Asn Ile Thr Ala Ala Asp Ala Asp Val
625                 630                 635                 640

His Pro Asn Ile Gly Pro Tyr Val Phe Glu Leu Pro Phe Val Pro Ala
                645                 650                 655

Ala Val Arg Lys Asn Trp Thr Ile Thr Arg Leu Asn Gly Asp Tyr Ala
                660                 665                 670

Gln Leu Ser Leu Arg Ile Leu Tyr Leu Glu Ala Gly Met Tyr Asp Val
                675                 680                 685

Pro Ile Ile Val Thr Asp Ser Gly Asn Pro Pro Leu Ser Asn Thr Ser
690                 695                 700

Ile Ile Lys Val Lys Val Cys Pro Cys Asp Asp Asn Gly Asp Cys Thr
705                 710                 715                 720

Thr Ile Gly Ala Val Ala Ala Gly Leu Gly Thr Gly Ala Ile Val
                725                 730                 735

Ala Ile Leu Ile Cys Ile Leu Ile Leu Leu Thr Met Val Leu Leu Phe
                740                 745                 750

Val Met Trp Met Lys Arg Arg Glu Lys Glu Arg His Thr Lys Gln Leu
                755                 760                 765

Leu Ile Asp Pro Glu Asp Asp Val Arg Glu Lys Ile Leu Lys Tyr Asp
                770                 775                 780

Glu Glu Gly Gly Gly Glu Glu Asp Gln Asp Tyr Asp Leu Ser Gln Leu
785                 790                 795                 800
```

```
Gln Gln Pro Glu Ala Met Gly His Val Pro Ser Lys Ala Pro Gly Val
            805                 810                 815

Arg Arg Val Asp Glu Arg Pro Val Gly Pro Glu Pro Gln Tyr Pro Ile
            820                 825                 830

Arg Pro Met Val Pro His Pro Gly Asp Ile Gly Asp Phe Ile Asn Glu
            835                 840                 845

Gly Leu Arg Ala Ala Asp Asn Asp Pro Thr Ala Pro Pro Tyr Asp Ser
            850                 855                 860

Leu Leu Val Phe Asp Tyr Glu Gly Ser Gly Ser Thr Ala Gly Ser Val
865                 870                 875                 880

Ser Ser Leu Asn Ser Ser Ser Gly Asp Gln Asp Tyr Asp Tyr Leu
                885                 890                 895

Asn Asp Trp Gly Pro Arg Phe Lys Lys Leu Ala Asp Met Tyr Gly Gly
                900                 905                 910

Gly Glu Glu Asp
        915

<210> SEQ ID NO 4
<211> LENGTH: 7
<212> TYPE: PRT
<213> ORGANISM: HOMO SAPIENS

<400> SEQUENCE: 4

Ile Asn Ser Met Ser Gly Arg
1               5

<210> SEQ ID NO 5
<211> LENGTH: 913
<212> TYPE: PRT
<213> ORGANISM: MUS MUSCULUS

<400> SEQUENCE: 5

Met Thr Thr Gly Ser Val Leu Pro Leu Leu Leu Gly Leu Ser Gly
1               5                   10                  15

Ala Leu Arg Ala His Arg Glu Asp Leu Thr Val Arg Glu Ala Cys Lys
            20                  25                  30

Ala Gly Phe Ser Glu Glu Gly Tyr Thr Ala Leu Ile Ser Pro Asn Val
        35                  40                  45

Leu Glu Gly Glu Lys Leu Leu Lys Val Glu Phe Ser Ser Cys Val Gly
    50                  55                  60

Thr Lys Gly Met Gln Tyr Glu Thr Asn Ser Leu Asp Phe Lys Val Gly
65                  70                  75                  80

Ala Asp Gly Thr Val Phe Ala Thr Arg Glu Leu Lys Ile Pro Ser Glu
                85                  90                  95

Gln Val Ala Phe Thr Val Thr Ala Arg Glu Arg Gln Ser Ala Glu Gln
            100                 105                 110

Trp Ala Ala Met Val Arg Leu Leu Val Ala Gln Thr Ser Ser Ala His
        115                 120                 125

Ser Glu His Lys Lys Gly Gln Thr Val Ala Leu Asp Pro Ser Gln Pro
    130                 135                 140

Pro Asn Asp Thr Leu Leu Pro Trp Pro Gln His Gln Ser Ser Gly Gly
145                 150                 155                 160

Leu Arg Arg Gln Lys Arg Asp Trp Val Ile Pro Pro Ile Asn Val Pro
                165                 170                 175

Glu Asn Ser Arg Gly Pro Phe Pro Gln Gln Leu Val Arg Ile Arg Ser
            180                 185                 190
```

-continued

```
Asp Lys Asp Asn Asp Ile Pro Ile Arg Tyr Ser Ile Thr Gly Val Gly
            195                 200                 205
Ala Asp Gln Pro Pro Met Glu Val Phe Asn Ile Asp Ser Met Ser Gly
    210                 215                 220
Arg Met Tyr Val Thr Arg Pro Met Asp Arg Glu Glu Arg Ala Ser Tyr
225                 230                 235                 240
His Leu Arg Ala His Ala Val Asp Met Asn Gly Asn Lys Val Glu Asn
                245                 250                 255
Pro Ile Asp Leu Tyr Ile Tyr Val Ile Asp Met Asn Asp Asn Arg Pro
            260                 265                 270
Glu Phe Ile Asn Gln Val Tyr Asn Gly Ser Val Asp Glu Gly Ser Lys
        275                 280                 285
Pro Gly Thr Tyr Val Met Thr Val Thr Ala Asn Asp Ala Asp Asp Ser
    290                 295                 300
Thr Thr Ala Asn Gly Met Val Arg Tyr Arg Ile Val Thr Gln Thr Pro
305                 310                 315                 320
Gln Ser Pro Ser Gln Asn Met Phe Thr Ile Asn Ser Glu Thr Gly Asp
                325                 330                 335
Ile Val Thr Val Ala Ala Gly Leu Asp Arg Glu Lys Val Gln Gln Tyr
            340                 345                 350
Thr Val Ile Val Gln Ala Thr Asp Met Glu Gly Asn Leu Asn Tyr Gly
        355                 360                 365
Leu Ser Asn Thr Ala Thr Ala Ile Ile Thr Val Thr Asp Val Asn Asp
    370                 375                 380
Asn Pro Pro Glu Phe Thr Thr Ser Thr Phe Ala Gly Glu Val Pro Glu
385                 390                 395                 400
Asn Arg Ile Glu Thr Val Val Ala Asn Leu Thr Val Met Asp Arg Asp
                405                 410                 415
Gln Pro His Ser Pro Asn Trp Asn Ala Val Tyr Arg Ile Ile Ser Gly
            420                 425                 430
Asp Pro Ser Gly His Phe Ser Val Arg Thr Asp Pro Val Thr Asn Glu
        435                 440                 445
Gly Met Val Thr Val Lys Ala Val Asp Tyr Glu Leu Asn Arg Ala
    450                 455                 460
Phe Met Leu Thr Val Met Val Ser Asn Gln Ala Pro Leu Ala Ser Gly
465                 470                 475                 480
Ile Gln Met Ser Phe Gln Ser Thr Ala Gly Val Thr Ile Ser Val Thr
                485                 490                 495
Asp Val Asn Glu Ala Pro Tyr Phe Pro Ser Asn His Lys Leu Ile Arg
            500                 505                 510
Leu Glu Glu Gly Val Pro Ala Gly Thr Ala Leu Thr Thr Phe Ser Ala
        515                 520                 525
Val Asp Pro Asp Arg Phe Met Gln Gln Ala Val Arg Tyr Ser Lys Leu
    530                 535                 540
Ser Asp Pro Ala Asn Trp Leu His Ile Asn Thr Ser Asn Gly Gln Ile
545                 550                 555                 560
Thr Thr Ala Ala Ile Leu Asp Arg Glu Ser Leu Tyr Thr Lys Asn Asn
                565                 570                 575
Val Tyr Glu Ala Thr Phe Leu Ala Ala Asp Asn Gly Ile Pro Pro Ala
            580                 585                 590
Ser Gly Thr Gly Thr Leu Gln Ile Tyr Leu Ile Asp Ile Asn Asp Asn
        595                 600                 605
```

-continued

```
Ala Pro Gln Leu Leu Pro Lys Glu Ala Gln Ile Cys Glu Arg Pro Gly
    610                 615                 620

Leu Asn Ala Ile Asn Ile Thr Ala Ala Asp Ala Asp Met Asp Pro Asn
625                 630                 635                 640

Ile Gly Pro Tyr Val Phe Glu Leu Pro Phe Ile Pro Thr Thr Val Arg
                645                 650                 655

Lys Asn Trp Thr Ile Thr Arg Leu Asn Gly Asp Tyr Ala Gln Leu Ser
            660                 665                 670

Leu Arg Ile Leu Tyr Leu Glu Ala Gly Val Tyr Asp Val Pro Ile Ile
        675                 680                 685

Val Thr Asp Ser Gly Asn Pro Pro Leu Ser Asn Thr Ser Val Ile Lys
    690                 695                 700

Val Lys Val Cys Pro Cys Asp Glu Asn Gly Asp Cys Thr Thr Val Gly
705                 710                 715                 720

Ala Val Ala Ala Ala Gly Leu Gly Thr Gly Ala Ile Val Ala Ile Leu
                725                 730                 735

Ile Cys Ile Val Ile Leu Leu Ile Met Val Leu Leu Phe Val Val Trp
            740                 745                 750

Met Lys Arg Arg Glu Lys Glu Arg His Thr Lys Gln Leu Leu Ile Asp
        755                 760                 765

Pro Glu Asp Asp Val Arg Asp Asn Ile Leu Lys Tyr Asp Glu Glu Gly
    770                 775                 780

Gly Gly Glu Glu Asp Gln Asp Tyr Asp Leu Ser Gln Leu Gln Gln Pro
785                 790                 795                 800

Glu Ala Met Glu His Val Leu Ser Lys Thr Pro Gly Val Arg Arg Val
                805                 810                 815

Asp Glu Arg Pro Val Gly Ala Glu Pro Gln Tyr Pro Val Arg Pro Val
            820                 825                 830

Val Pro His Pro Gly Asp Ile Gly Asp Phe Ile Asn Glu Gly Leu Arg
        835                 840                 845

Ala Ala Asp Asn Asp Pro Thr Ala Pro Pro Tyr Asp Ser Leu Leu Val
    850                 855                 860

Phe Asp Tyr Glu Gly Ser Gly Ser Thr Ala Gly Ser Val Ser Ser Leu
865                 870                 875                 880

Asn Ser Ser Ser Gly Asp Gln Asp Tyr Asp Tyr Leu Asn Asp Trp
                885                 890                 895

Gly Pro Arg Phe Lys Lys Leu Ala Asp Met Tyr Gly Gly Gly Glu Glu
            900                 905                 910

Asp
```

```
<210> SEQ ID NO 6
<211> LENGTH: 6
<212> TYPE: PRT
<213> ORGANISM: Artificial Sequence
<220> FEATURE:
<223> OTHER INFORMATION: CADHERIN ANTAGONIST
<220> FEATURE:
<221> NAME/KEY: VARIANT
<222> LOCATION: 2
<223> OTHER INFORMATION: Xaa = Asp, Asn, Glu or Gln

<400> SEQUENCE: 6

Ile Xaa Ser Met Gly Arg
 1               5

<210> SEQ ID NO 7
<211> LENGTH: 5
```

-continued

```
<212> TYPE: PRT
<213> ORGANISM: Artificial Sequence
<220> FEATURE:
<223> OTHER INFORMATION: CADHERIN ANTAGONIST
<220> FEATURE:
<221> NAME/KEY: VARIANT
<222> LOCATION: 3
<223> OTHER INFORMATION: Xaa = Asp, Asn, Glu or Gln

<400> SEQUENCE: 7

Cys Ile Xaa Ser Cys
 1               5

<210> SEQ ID NO 8
<211> LENGTH: 5
<212> TYPE: PRT
<213> ORGANISM: Artificial Sequence
<220> FEATURE:
<223> OTHER INFORMATION: CYCLIC CADHERIN ANTAGONIST, DISULFIDE BOND
      BETWEEN Cys1 and Cys5

<400> SEQUENCE: 8

Cys Ile Asp Ser Cys
 1               5

<210> SEQ ID NO 9
<211> LENGTH: 5
<212> TYPE: PRT
<213> ORGANISM: Artificial Sequence
<220> FEATURE:
<223> OTHER INFORMATION: CYCLIC CADHERIN ANTAGONIST, DISULFIDE BOND
      BETWEEN Cys1 and Cys5

<400> SEQUENCE: 9

Cys Ile Asn Pro Cys
 1               5

<210> SEQ ID NO 10
<211> LENGTH: 7
<212> TYPE: PRT
<213> ORGANISM: Artificial Sequence
<220> FEATURE:
<223> OTHER INFORMATION: CADHERIN ANTAGONIST

<400> SEQUENCE: 10

Ile Asp Ser Ala Ser Gly Arg
 1               5

<210> SEQ ID NO 11
<211> LENGTH: 7
<212> TYPE: PRT
<213> ORGANISM: Artificial Sequence
<220> FEATURE:
<223> OTHER INFORMATION: CADHERIN ANTAGONIST

<400> SEQUENCE: 11

Ile Asn Pro Ala Ser Gly Gln
 1               5

<210> SEQ ID NO 12
<211> LENGTH: 5
<212> TYPE: PRT
<213> ORGANISM: Artificial Sequence
<220> FEATURE:
<223> OTHER INFORMATION: CYCLIC CADHERIN ANTAGONIST, DISULFIDE BOND
      BETWEEN Cys1 and Cys5

<400> SEQUENCE: 12
```

```
Cys Ser Asp Ile Cys
1               5

<210> SEQ ID NO 13
<211> LENGTH: 5
<212> TYPE: PRT
<213> ORGANISM: Artificial Sequence
<220> FEATURE:
<223> OTHER INFORMATION: CYCLIC CADHERIN ANTAGONIST, DISULFIDE BOND
      BETWEEN Cys1 and Cys5

<400> SEQUENCE: 13

Cys Arg Ala Asp Cys
1               5

<210> SEQ ID NO 14
<211> LENGTH: 69
<212> TYPE: PRT
<213> ORGANISM: MUS MUSCULUS

<400> SEQUENCE: 14

Ile Arg Ser Asp Arg Asp Lys Asn Leu Ser Leu Arg Tyr Ser Val Thr
1               5                   10                  15

Gly Pro Gly Ala Asp Gln Pro Pro Thr Gly Ile Phe Ile Ile Asn Pro
            20                  25                  30

Ile Ser Gly Gln Leu Ser Val Thr Lys Pro Leu Asp Arg Glu Leu Ile
        35                  40                  45

Ala Arg Phe His Leu Arg Ala His Ala Val Asp Ile Asn Gly Asn Gln
    50                  55                  60

Val Glu Asn Pro Ile
65

<210> SEQ ID NO 15
<211> LENGTH: 69
<212> TYPE: PRT
<213> ORGANISM: MUS MUSCULUS

<400> SEQUENCE: 15

Ile Arg Ser Asp Lys Asp Asn Asp Ile Pro Ile Arg Tyr Ser Ile Thr
1               5                   10                  15

Gly Val Gly Ala Asp Gln Pro Pro Met Glu Val Phe Asn Ile Asp Ser
            20                  25                  30

Met Ser Gly Arg Met Tyr Val Thr Arg Pro Met Asp Arg Glu Glu Arg
        35                  40                  45

Ala Ser Tyr His Leu Arg Ala His Ala Val Asp Met Asn Gly Asn Lys
    50                  55                  60

Val Glu Asn Pro Ile
65

<210> SEQ ID NO 16
<211> LENGTH: 69
<212> TYPE: PRT
<213> ORGANISM: RATUS NORWEGICUS

<400> SEQUENCE: 16

Ile Arg Ser Asp Lys Asp Asn Asp Ile Pro Ile Arg Tyr Ser Ile Thr
1               5                   10                  15

Gly Val Gly Ala Asp Gln Pro Pro Met Glu Val Phe Asn Ile Asp Ser
            20                  25                  30

Met Ser Gly Arg Met Tyr Val Thr Arg Pro Met Asp Arg Glu Glu Arg
        35                  40                  45
```

-continued

```
Ala Ser Tyr His Leu Arg Ala His Ala Val Asp Met Asn Gly Asn Lys
        50                  55                  60

Val Glu Asn Pro Ile
 65

<210> SEQ ID NO 17
<211> LENGTH: 69
<212> TYPE: PRT
<213> ORGANISM: HOMO SAPIENS

<400> SEQUENCE: 17

Ile Arg Ser Asp Lys Asp Asn Asp Ile Pro Ile Arg Tyr Ser Ile Thr
  1               5                  10                  15

Gly Val Gly Ala Asp Gln Pro Pro Met Glu Val Phe Ser Ile Asp Ser
                 20                  25                  30

Met Ser Gly Arg Met Tyr Val Thr Arg Pro Met Asp Arg Glu Glu His
             35                  40                  45

Ala Ser Tyr His Leu Arg Ala His Ala Val Asp Met Asn Gly Asn Lys
        50                  55                  60

Val Glu Asn Pro Ile
 65

<210> SEQ ID NO 18
<211> LENGTH: 69
<212> TYPE: PRT
<213> ORGANISM: HOMO SAPIENS

<400> SEQUENCE: 18

Ile Arg Ser Asp Lys Asp Asn Asp Ile Pro Ile Arg Tyr Ser Ile Thr
  1               5                  10                  15

Gly Val Gly Ala Asp Gln Pro Pro Met Glu Val Phe Ser Ile Asn Ser
                 20                  25                  30

Met Ser Gly Arg Met Tyr Val Thr Arg Pro Met Asp Arg Glu Glu His
             35                  40                  45

Ala Ser Tyr His Leu Arg Ala His Ala Val Asp Met Asn Gly Asn Lys
        50                  55                  60

Val Glu Asn Pro Ile
 65

<210> SEQ ID NO 19
<211> LENGTH: 69
<212> TYPE: PRT
<213> ORGANISM: GALLUS GALLUS

<400> SEQUENCE: 19

Ile Arg Ser Asp Lys Asp Lys Glu Ile His Ile Arg Tyr Ser Ile Thr
  1               5                  10                  15

Gly Val Gly Ala Asp Gln Pro Pro Met Glu Val Phe Ser Ile Asp Pro
                 20                  25                  30

Val Ser Gly Arg Met Tyr Val Thr Arg Pro Met Asp Arg Glu Glu Arg
             35                  40                  45

Ala Ser Tyr His Leu Arg Ala His Ala Val Asp Met Asn Gly Asn Lys
        50                  55                  60

Val Glu Asn Pro Ile
 65

<210> SEQ ID NO 20
<211> LENGTH: 5
```

```
-continued

<212> TYPE: PRT
<213> ORGANISM: Artificial Sequence
<220> FEATURE:
<223> OTHER INFORMATION: CYCLIC CADHERIN ANTAGONIST, DISULFIDE BOND
      BETWEEN Cys1 and Cys5

<400> SEQUENCE: 20

Cys His Ala Val Cys
1               5
```